(12) United States Patent
Okada

(10) Patent No.: US 8,747,316 B2
(45) Date of Patent: Jun. 10, 2014

(54) IN VIVO COMPONENT MEASUREMENT METHOD, DATA PROCESSING METHOD FOR IN VIVO COMPONENT MEASUREMENT, IN VIVO COMPONENT MEASUREMENT APPARATUS AND COLLECTION MEMBER

(75) Inventor: Seiki Okada, Kobe (JP)

(73) Assignee: Sysmex Corporation, Kobe (JP)

( * ) Notice: Subject to any disclaimer, the term of this patent is extended or adjusted under 35 U.S.C. 154(b) by 523 days.

(21) Appl. No.: 13/016,088

(22) Filed: Jan. 28, 2011

(65) Prior Publication Data

US 2011/0124998 A1 May 26, 2011

Related U.S. Application Data

(63) Continuation of application No. PCT/JP2009/063668, filed on Jul. 31, 2009.

(30) Foreign Application Priority Data

Jul. 31, 2008 (JP) ................. 2008-198940
Dec. 12, 2008 (JP) ................. 2008-317017
Mar. 27, 2009 (JP) ................. 2009-078652

(51) Int. Cl.
*A61B 5/00* (2006.01)
(52) U.S. Cl.
USPC ............ 600/365; 600/316; 600/347; 600/362
(58) Field of Classification Search
USPC ................... 600/316, 347, 362, 364, 365
See application file for complete search history.

(56) References Cited

U.S. PATENT DOCUMENTS

| | | | |
|---|---|---|---|
| 4,821,733 A | 4/1989 | Peck | |
| 5,279,543 A | 1/1994 | Glikfeld et al. | |
| 5,362,307 A | 11/1994 | Guy et al. | |
| 5,730,714 A | 3/1998 | Guy et al. | |
| 6,190,315 B1 | 2/2001 | Kost et al. | |
| 6,542,765 B1 | 4/2003 | Guy et al. | |
| 6,714,815 B2 | 3/2004 | Guy et al. | |
| 7,018,345 B2 | 3/2006 | Mori et al. | |

(Continued)

FOREIGN PATENT DOCUMENTS

| | | |
|---|---|---|
| JP | 01-163666 A | 6/1989 |
| JP | 04-502561 A | 5/1992 |

(Continued)

OTHER PUBLICATIONS

Yingxia, Zhou et al., "The influence of slow-release starch containing enteral nutrition on blood glucose and insulin response in type 2 diabetic patients," Shanghai Medical Journal, vol. 27, No. 2, 2004, pp. 116-118 (with English translation).

(Continued)

*Primary Examiner* — Navin Natnithithadha
*Assistant Examiner* — Etsub Berhanu
(74) *Attorney, Agent, or Firm* — Brinks Gilson & Lione

(57) ABSTRACT

An in vivo component measurement method allowing how long a high concentration state of a measurement target component continues in an organism to be grasped is provided. In this in vivo component measurement method, a value relating to an amount of a measurement target component in tissue fluid extracted for 60 minutes or more from an organism on which a treatment for enhancing extraction of tissue fluid has been made is acquired.

19 Claims, 27 Drawing Sheets

(56) References Cited

U.S. PATENT DOCUMENTS

| | | |
|---|---|---|
| 7,066,884 B2 | 6/2006 | Custer et al. |
| 2002/0026110 A1* | 2/2002 | Parris et al. .................. 600/347 |
| 2004/0171980 A1 | 9/2004 | Mitragotri et al. |
| 2004/0236268 A1 | 11/2004 | Mitragotri et al. |
| 2005/0096520 A1* | 5/2005 | Maekawa et al. ............. 600/365 |
| 2006/0015058 A1 | 1/2006 | Kellogg et al. |
| 2006/0063218 A1* | 3/2006 | Bartkowiak et al. ............ 435/14 |
| 2006/0094944 A1 | 5/2006 | Chuang |
| 2006/0094945 A1 | 5/2006 | Barman et al. |
| 2006/0094946 A1 | 5/2006 | Kellogg et al. |
| 2006/0206011 A1* | 9/2006 | Higgins et al. ................ 600/300 |
| 2007/0142721 A1 | 6/2007 | Berner et al. |
| 2007/0232875 A1 | 10/2007 | Maekawa et al. |
| 2008/0112984 A1* | 5/2008 | Schulte et al. ................. 424/400 |
| 2008/0311670 A1 | 12/2008 | Zhu |

FOREIGN PATENT DOCUMENTS

| | | |
|---|---|---|
| JP | 09-503924 A | 4/1997 |
| JP | 2004-195218 A | 7/2004 |
| JP | 2007-260315 A | 10/2007 |
| JP | 2008-518662 A | 6/2008 |
| WO | WO 89/06989 A1 | 8/1989 |
| WO | WO 95/02357 A1 | 1/1995 |
| WO | WO 01/70330 A2 | 9/2001 |

OTHER PUBLICATIONS

Office Action from counterpart Chinese Application No. 200980129269.7, dated Apr. 20, 2012, 9 pages (with English translation).

International Search Report for International Application No. PCT/JP2009/063668, dated Sep. 8, 2009, 1 page.

Extended European Search Report for European Application No. 09803046.3, dated Dec. 21, 2012, 9 pages.

* cited by examiner

IN VIVO COMPONENT MEASUREMENT METHOD, DATA PROCESSING METHOD FOR IN VIVO COMPONENT MEASUREMENT, IN VIVO COMPONENT MEASUREMENT APPARATUS AND COLLECTION MEMBER

RELATED APPLICATIONS

This application is a continuation of PCT/JP2009/063668 filed on Jul. 31, 2009, which claims priority to Japanese Application Nos. 2008-198940 filed on Jul. 31, 2008, 2008-317017 filed on Dec. 12, 2008, and 2009-078652 filed on Mar. 27, 2009. The entire contents of these applications are incorporated herein by reference.

BACKGROUND OF THE INVENTION

1. Field of the Invention

The present invention relates to an in vivo component measurement method, a data processing method for in vivo component measurement, an in vivo component measurement apparatus and a collection member.

2. Description of the Background Art

Japanese Patent Laying-Open No. 2004-195218 discloses an iontophoresis device comprising a pair of electrode assemblies applied to the oral mucosa and the skin and a pad for extraction provided on the electrode assembly applied to the oral mucosa. This iontophoresis device is so formed that glucose can be extracted from the oral mucosa into the pad for extraction by so-called iontophoresis action by applying electric energy to a site sandwiched between the pair of electrode assemblies for a prescribed time (30 seconds to 20 minutes). The quantity of the glucose extracted into the pad for extraction can be determined by a detector. This iontophoresis device can measure the quantity of glucose in the body in a short time of 30 seconds to 20 minutes by applying electric energy to an organism.

Blood glucose (blood sugar) is measured in a fasting state or after meal (after glucose load), whereby effective information for diabetes diagnosis can be provided. A blood glucose level in a fasting state is used in the diagnosis of diabetes of a subject, for example. A blood glucose level after glucose load serves as an index for knowing how long a high blood glucose state continues after glucose load and is useful in screening so-called hidden diabetes in which decline of a blood glucose level after glucose load is slow.

However, Japanese Patent Laying-Open No. 2004-195218 does not describe grasping how long a high blood glucose state continues at all.

SUMMARY OF THE INVENTION

The present invention has been proposed in order to solve the aforementioned problems, and an object of the present invention is to provide an in vivo component measurement method and an in vivo component measurement apparatus both allowing how long a high concentration state of a measurement target component continues in an organism to be grasped, a collection member used in an in vivo component measurement apparatus and a data processing method for in vivo component measurement.

In order to attain the aforementioned object, an in vivo component measurement method according to a first aspect of the present invention comprises preparing tissue fluid extracted for 60 minutes or more from an organism on which a treatment for enhancing extraction of tissue fluid has been made, and acquiring a value relating to an amount of a measurement target component in the extracted tissue fluid.

In this in vivo component measurement method according to the first aspect, as hereinabove described, the extraction of tissue fluid from the organism is enhanced, whereby the tissue fluid can be easily extracted from the organism. Further, the tissue fluid is extracted from the organism while spending a sufficient time of 60 minutes or more and the amount of the measurement target component in the extracted tissue fluid is acquired, whereby an amount correlating with the total amount of the measurement target component circulating in the organism within an extraction time can be acquired. The total amount of the measurement target component circulating in the organism within the extraction time correlates with a value obtained by integrating a concentration of the measurement target component in the organism in the time, and hence how long a high concentration state of the measurement target component continues in the organism can be grasped based on the acquired amount.

In the aforementioned in vivo component measurement method according to the first aspect, the treatment is preferably made by forming fine pores on a skin of the organism, and the extraction is preferably performed through the skin where the fine pores are formed. According to this structure, the tissue fluid can be easily extracted through a site of the skin where the fine pores are formed.

In the aforementioned in vivo component measurement method according to the first aspect, the extraction is preferably performed by extracting tissue fluid to an extraction medium containing a hypertonic aqueous solution having a higher osmotic pressure than pure water. According to this structure, movement of the tissue fluid to the extraction medium is enhanced by the osmotic pressure of the hypertonic aqueous solution higher than that of pure water, and hence the movement of the tissue fluid to the extraction medium can be further enhanced as compared with a case of using an extraction medium containing pure water. Thus, the amount of the measurement target component extracted per unit time can be increased, and hence measurement errors can be reduced as compared with a case of a small amount of the measurement target component.

In this case, the hypertonic aqueous solution preferably contains an auxiliary component other than the measurement target component, the auxiliary component being contained with the measurement target component in the tissue fluid. According to this structure, the hypertonic aqueous solution having a higher osmotic pressure than pure water can be obtained using the auxiliary component without changing the amount of the measurement target component. Movement of the tissue fluid to the extraction medium can be enhanced without changing measurement results of the measurement target component by using this hypertonic aqueous solution.

In the aforementioned structure in which the hypertonic aqueous solution contains the auxiliary component, the auxiliary component is preferably at least one selected from a group consisting of kalium chloride, glycine and urea. According to this structure, the hypertonic aqueous solution having a higher osmotic pressure than pure water can be obtained using at least one of kalium chloride, glycine and urea contained in the tissue fluid in a slight amount. Thus, the hypertonic aqueous solution having a higher concentration (osmotic pressure) than the auxiliary component in the tissue fluid can be easily obtained.

In this case, a concentration of the auxiliary component in the hypertonic aqueous solution is preferably 0.2 mmol/L or more. According to this structure, the concentration (osmotic pressure) of the hypertonic aqueous solution containing at least one of kalium chloride, glycine and urea can be rendered higher than the concentrations of kalium chloride, glycine and urea each contained in the tissue fluid in a slight amount and each having few differences in the content thereof in the tissue fluid among individuals. Thus, movement of the tissue fluid to the extraction medium can be further enhanced due to the higher concentration (osmotic pressure) of the auxiliary component in the hypertonic aqueous solution than the auxiliary component in the tissue fluid.

In the aforementioned in vivo component measurement method according to the first aspect, a time for extracting the tissue fluid is preferably 120 minutes or more. According to this structure, the measurement target component, the amount of which reflects conditions of circulation of the measurement target component generated in the organism across a more sufficient time, is accumulated as compared with a case where the tissue fluid is extracted for at least 60 minutes and less than 120 minutes. Thus, the conditions of circulation of the measurement target component generated in the organism in a longer time can be predicted based on a value relating to the amount of the obtained measurement target component.

In the aforementioned in vivo component measurement method according to the first aspect, the time for extracting the tissue fluid is preferably 180 minutes or more. According to this structure, the measurement target component, the amount of which reflects conditions of circulation of the measurement target component generated in the organism across a more sufficient time, is accumulated as compared with a case where the tissue fluid is extracted for at least 60 minutes and less than 180 minutes. Thus, the conditions of circulation of the measurement target component generated in the organism in a longer time can be predicted based on a value relating to the amount of the obtained measurement target component.

In the aforementioned in vivo component measurement method according to the first aspect, the measurement target component is preferably glucose. According to this structure, a value reflecting the total quantity of glucose circulating in the organism within the extraction time can be measured, and how long a high blood glucose state of a subject continues can be grasped.

The aforementioned in vivo component measurement method according to the first aspect preferably further comprises acquiring an integrated value of a concentration of the measurement target component in an organism, corresponding to an extraction time of tissue fluid based on the value relating to the amount of the measurement target component. According to this structure, this integrated value is a value obtained by integrating the concentration of the measurement target component in the organism in the extraction time, and hence how long a high concentration state of the measurement target component continues in the organism can be grasped based on this integrated value.

The aforementioned method in which the integrated value is acquired preferably further comprises acquiring an amount of an electrolyte contained in extracted tissue fluid, wherein the integrated value is acquired based on the value relating to the amount of the measurement target component and the amount of the electrolyte. According to this structure, the ease of extracting the tissue fluid can be predicted based on a detected value of the electrolyte plentifully existing in the organism. In other words, the amounts of the measurement target component and the electrolyte in the extracted tissue fluid both change depending on the condition of the skin or the like (ease of extraction), and hence a large amount of the electrolyte contained in the extracted tissue fluid is considered to indicate a good skin condition for the extraction of the tissue fluid, whereas a low amount of the extracted electrolyte is considered to indicate a poor skin condition for the extraction of the tissue fluid. Therefore, the value relating to the amount of the measurement target component is acquired based on the detection value of the measurement target component and the detection value of the electrolyte, whereby the ease of extracting the tissue fluid is added, and a value more accurately reflecting the total amount of the measurement target component circulating in the organism in the extraction time can be acquired.

In the aforementioned in vivo component measurement method according to the first aspect, the integrated value is preferably a value corresponding to an area under the curve (AUC) of a blood concentration time curve of the measurement target component. The AUC is an area under the concentration curve of the measurement target component in the organism, and hence a value thereof is increased if a high concentration state of the measurement target component continues for a long time within the extraction time, and a value thereof is decreased if a high concentration state of the measurement target component continues only for a short time. Therefore, how long a high concentration state of the measurement target component continues in the organism can be directly measured by obtaining the AUC.

The aforementioned method in which the value corresponding to the area under the blood concentration time curve of the measurement target component is acquired preferably further comprises acquiring a value obtained by dividing the value corresponding to an AUC of the measurement target component by a time for extraction. According to this structure, a value corresponding to the area under the blood concentration time curve per unit time can be obtained, and hence those values can be easily compared with each other even in a case where the extraction times are different from each other.

The aforementioned in vivo component measurement method according to the first aspect preferably further comprises informing a subject of an end of extraction when a prescribed time of 60 minutes or more elapses from a start of extraction of the tissue fluid. According to this structure, it is possible for the subject to know the end of extraction by a notice, and hence it is possible to control a difference between the extraction time and the scheduled time.

An in vivo component measurement apparatus according to a second aspect of the present invention comprises a set portion for setting a collection member capable of accumulating a measurement target component in tissue fluid extracted for 60 minutes or more from an organism on which a treatment for enhancing extraction of tissue fluid has been made, and a detection portion for acquiring a value relating to an amount of the measurement target component accumulated by the collection member set on the set portion.

In this in vivo component measurement apparatus according to the second aspect, as hereinabove described, the extraction of tissue fluid from the organism is enhanced, whereby the tissue fluid can be easily extracted from the organism. Further, the collection member having accumulated the tissue fluid extracted from the organism while spending a sufficient time of 60 minutes or more is set on the set portion, whereby the amount of the measurement target component in the extracted tissue fluid can be acquired. Thus, an amount correlating with the total amount of the measurement target component circulating in the organism within an extraction time can be acquired. The total amount of the measurement target component circulating in the organism within the extraction time correlates with a value obtained by integrating a concentration of the measurement target component in the organism in the time, and hence how long a high concentration state of the measurement target component continues in the organism can be grasped based on the acquired amount.

In the aforementioned in vivo component measurement apparatus according to the second aspect, the measurement target component is preferably glucose. According to this structure, a value reflecting the total quantity of glucose circulating in the organism within the extraction time can be acquired, and this measurement value can be used for grasping clinical conditions of diabetes and so on.

The aforementioned in vivo component measurement apparatus according to the second aspect preferably further comprises an analysis portion acquiring an integrated value of a concentration of the measurement target component in the organism, corresponding to an extraction time of tissue fluid based on the value relating to an amount of the measurement target component. According to this structure, the integrated value is acquired by the analysis portion, whereby this integrated value is a value obtained by integrating a concentration of the measurement target component in the organism in the extraction time, and hence how long a high concentration state of the measurement target component continues in the organism can be grasped based on this integrated value.

In this case, the integrated value is preferably a value corresponding to an area under the blood concentration time curve (AUC) of a measurement target component. According to this structure, the AUC is an area under the concentration curve of the measurement target component in the organism, and hence a value thereof is increased if a high concentration state of the measurement target component continues for a long time within the extraction time, and a value thereof is decreased if a high concentration state of the measurement target component continues only for a short time. Therefore, how long a high concentration state of the measurement target component continues in the organism can be directly measured by obtaining the AUC.

A collection member according to a third aspect of the present invention is used in an in vivo component measurement apparatus for extracting tissue fluid from an organism on which extraction of tissue fluid has been enhanced and acquiring a value relating to an amount of a measurement target component in extracted tissue fluid, and includes an extraction medium capable of accumulating the measurement target component in tissue fluid extracted for 60 minutes or more from the organism.

In the collection member according to the third aspect, as hereinabove described, the extraction of tissue fluid from the organism is enhanced, whereby the tissue fluid can be easily extracted from the organism. Further, the tissue fluid extracted from the organism while spending a sufficient time of 60 minutes or more can be accumulated in the extraction medium by the collection member, and hence the amount of the measurement target component in the extracted tissue fluid can be acquired by measuring the tissue fluid accumulated in the extraction medium. Thus, an amount correlating with the total amount of the measurement target component circulating in the organism within an extraction time can be acquired. The total amount of the measurement target component circulating in the organism within the extraction time correlates with a value obtained by integrating a concentration of the measurement target component in the organism in the time, and hence how long a high concentration state of the measurement target component continues in the organism can be grasped based on the acquired amount.

In the aforementioned collection member according to the third aspect, the extraction medium is preferably a gel. According to this structure, the tissue fluid is spontaneously extracted by applying the gel to the skin, and the measurement target component is accumulated in the gel. Thus, the measurement target component can be easily accumulated, and hence the measurement operation can be simplified.

In this case, the gel preferably contains a hypertonic aqueous solution having a higher osmotic pressure than pure water. According to this structure, movement of the tissue fluid to the extraction medium is enhanced by the osmotic pressure of the hypertonic aqueous solution higher than that of pure water, and hence movement of the tissue fluid to the gel can be further enhanced as compared with a case of using a gel containing pure water. Thus, the amount of the measurement target component extracted per unit time can be increased, and hence measurement errors can be reduced as compared with a case of a small amount of the measurement target component.

In the aforementioned structure in which the gel contains the hypertonic aqueous solution having a higher osmotic pressure than pure water, the hypertonic aqueous solution preferably contains an auxiliary component other than the measurement target component, contained with the measurement target component in the tissue fluid. According to this structure, the hypertonic aqueous solution having a higher osmotic pressure than pure water can be obtained using the auxiliary component without changing the amount of the measurement target component. Movement of the tissue fluid to the extraction medium can be enhanced without changing measurement results of the measurement target component by using this hypertonic aqueous solution.

In this case, the auxiliary component is preferably at least one selected from a group consisting of kalium chloride, glycine and urea. According to this structure, the hypertonic aqueous solution having a higher osmotic pressure than pure water can be obtained using at least one of kalium chloride, glycine and urea contained in the tissue fluid in a slight amount. Thus, the hypertonic aqueous solution having a higher concentration (osmotic pressure) than the auxiliary component in the tissue fluid can be easily obtained.

In the aforementioned case where the auxiliary component is at least one selected from a group consisting of kalium chloride, glycine and urea, a concentration of the auxiliary component in the hypertonic aqueous solution is preferably 0.2 mmol/L or more. According to this structure, the concentration (osmotic pressure) of the hypertonic aqueous solution containing at least one of kalium chloride, glycine and urea can be rendered higher than the concentrations of kalium chloride, glycine and urea each contained in the tissue fluid in a slight amount and each having few differences in the content thereof in the tissue fluid among individuals. Thus, movement of the tissue fluid to the extraction medium can be further enhanced due to the higher concentration (osmotic pressure) of the auxiliary component in the hypertonic aqueous solution than the auxiliary component in the tissue fluid.

An in vivo component measurement method according to a fourth aspect of the present invention comprises accumulating a measurement target component in tissue fluid extracted for 60 minutes or more from an organism on which a treatment for enhancing extraction of tissue fluid has been made with converting the measurement target component into a component for accumulation different from the measurement target component, and acquiring a value relating to an amount of the measurement target component based on an amount of the accumulated component for accumulation.

In this in vivo component measurement method according to the fourth aspect, as hereinabove described, the extraction of tissue fluid from the organism is enhanced, whereby the tissue fluid can be easily extracted from the organism. Further, the measurement target component in the tissue fluid is converted into the component for accumulation different from the measurement target component to be accumulated while spending a sufficient time of 60 minutes or more, and the amount of the measurement target component in the extracted tissue fluid is acquired based on the amount of the accumulated component for accumulation, whereby an amount correlating with the total amount of the measurement target component circulating in the organism within an extraction time can be acquired. The total amount of the measurement target component circulating in the organism within the extraction time correlates with a value obtained by integrating a concentration of the measurement target component in the organism in the time, and hence how long a high concentration state of the measurement target component continues in the organism can be grasped based on the acquired amount.

A data processing method for in vivo component measurement according to a fifth aspect of the present invention comprises acquiring a value relating to an amount of a measurement target component in tissue fluid extracted for 60 minutes or more from an organism on which a treatment for enhancing extraction of tissue fluid has been made, and acquiring an integrated value of the measurement target component concentration in an organism, corresponding to an extraction time based on the acquired value.

In this data processing method for in vivo component measurement according to the fifth aspect, as hereinabove described, the extraction of tissue fluid from the organism is enhanced, whereby the tissue fluid can be easily extracted from the organism. Further, the tissue fluid is extracted from the organism while spending a sufficient time of 60 minutes or more and the amount of the measurement target component in the extracted tissue fluid is acquired, whereby an integrated value of a measurement target component concentration in the organism, corresponding to the extraction time of the tissue fluid can be acquired based on the acquired value. This integrated value is a value obtained by integrating the concentration of the measurement target component in the organism in the extraction time, and hence how long a high concentration state of the measurement target component continues in the organism can be grasped based on this integrated value.

In the aforementioned data processing method for in vivo component measurement according to the fifth aspect, the integrated value is preferably an area under the blood concentration time curve (AUC) of a measurement target component. The AUC is an area under the concentration curve of the measurement target component in the organism, and hence a value thereof is increased if a high concentration state of the measurement target component continues for a long time within the extraction time, and a value thereof is decreased if a high concentration state of the measurement target component continues only for a short time. Therefore, how long a high concentration state of the measurement target component continues in the organism can be directly measured by obtaining the AUC.

DETAILED DESCRIPTION OF THE PREFERRED EMBODIMENTS

Figure 1:
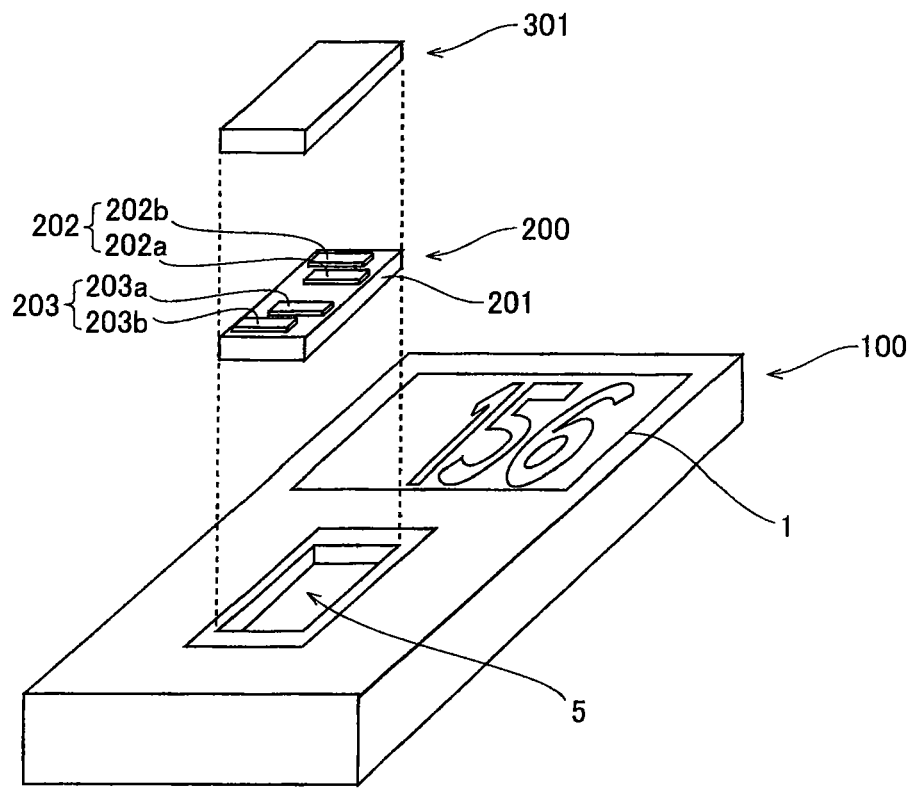
FIG. 1 is a perspective view showing a measurement apparatus, a sensor chip and a collection member which are used in a blood glucose AUC measurement method according to a first embodiment of the present invention.

Embodiments of the present invention are hereinafter described with reference to the drawings.

In the following embodiments, examples where the present invention is applied to measurement of blood glucose AUC are described. The blood glucose AUC refers to an area (unit: mg·h/dl) of a portion which is enclosed with a curve and a horizontal axis described by a graph representing time lapse of a blood glucose level. The blood glucose AUC is an index used for effect determination of insulin and oral drugs in medical treatments of diabetes. For example, a value reflecting a total quantity of glucose (blood glucose) circulating in the blood within a prescribed period after sugar load (after meal) is measured by the blood glucose AUC so that a total quantity of glucose circulating in the body of a subject after sugar load can be predicted. The total quantity of glucose circulating in the body of the subject after sugar load is very useful information for knowing how long a high blood glucose state due to sugar load continues. For example, the total quantity of glucose circulating in the body of the subject after sugar load serves as a clue for knowing insulin secretion response rate after sugar load or a clue for knowing effects of diabetes oral drugs and insulin when the subject receives diabetes those.

Significance of measuring the blood glucose AUC in this manner is that it is possible to control influences of personal differences in glucose metabolism in a glucose tolerance evaluation based on blood glucose measurement at a point in time by measuring the blood glucose AUC. In other words, because there are personal differences in time required for a response to sugar load to appear in the blood glucose level, it is impossible to grasp whether the blood glucose level is in rise time or in peak time, simply by measuring the blood glucose level at a certain time after the sugar load. Further, even if it is possible to measure the blood glucose level at the peak time, it is impossible to grasp how long a high blood glucose state continues. Recently, a disease referred to as "hidden diabetes" is watched with interest, and this disease is characterized in that increase of a blood glucose level after meal is rapid or a rate of decrease of a blood glucose level after increase is slow although a blood glucose level in a fasting state is normal or slightly high, and a high blood glucose state continues for a long time as compared with a healthy subject. Thus, how long a high blood glucose state continues cannot be obtained by blood glucose measurement at a point in time, and naturally information useful for screening of hidden diabetes cannot be provided by blood glucose measurement at a point in time. In this respect, through the blood glucose AUC measurement, it is possible to obtain a value reflecting a total quantity of blood glucose circulating in the blood within a prescribed period. Therefore, the measurement value is not affected by time required for a response to sugar load to appear in the blood glucose level, and further it is possible to predict how long the high blood glucose state continues based on the measurement value. Thus, it is possible to obtain a value useful for prediction of glucose tolerance due to sugar load by measuring the blood glucose AUC, without influence of personal differences in glucose metabolism.

For measuring the blood glucose AUC, ordinarily, the blood is drawn every prescribed time interval (every 30 minutes, for example) and blood glucose levels of the drawn blood are obtained. Subsequently, a graph representing time lapse of the blood glucose level is obtained and an area of a pardon enclosed with a curve and a horizontal axis described by the graph is obtained so that the blood glucose AUC is obtained. A value obtained using each of blood glucose AUC measurement methods according to the following embodiments is available for determination of diabetes instead of the blood glucose AUC by such blood drawing.

First Embodiment

First, the structures of a measurement apparatus, a sensor chip, a collection member and a puncture device which are used in a blood glucose AUG measurement method according to a first embodiment of the present invention are described with reference to FIGS. 1 to 9.

[Structure of Measurement Apparatus]

Figure 2:
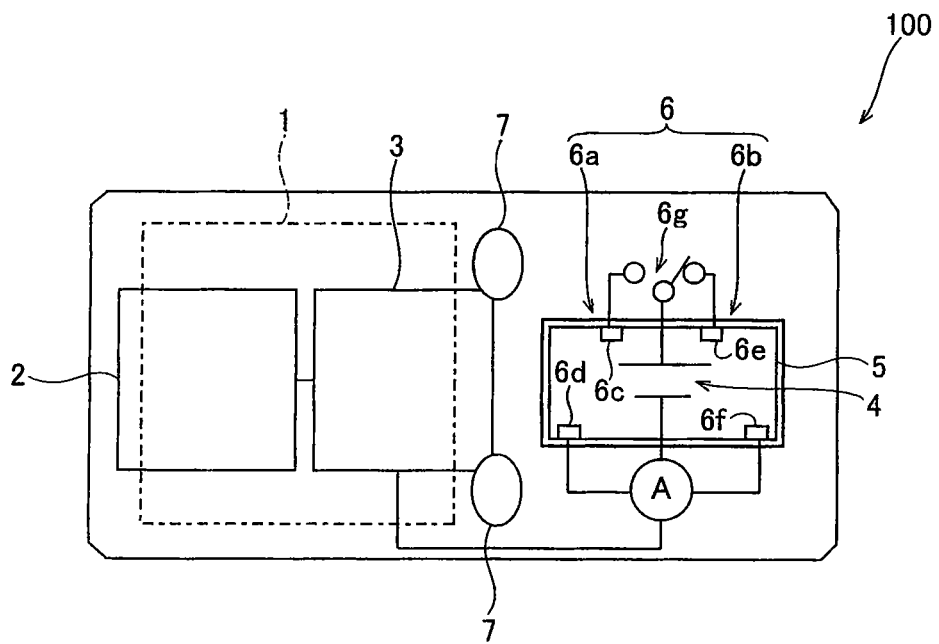
FIG. 2 is a schematic plan view showing the measurement apparatus used in the blood glucose AUC measurement method according to the first embodiment shown in FIG. 1.
Figure 3:
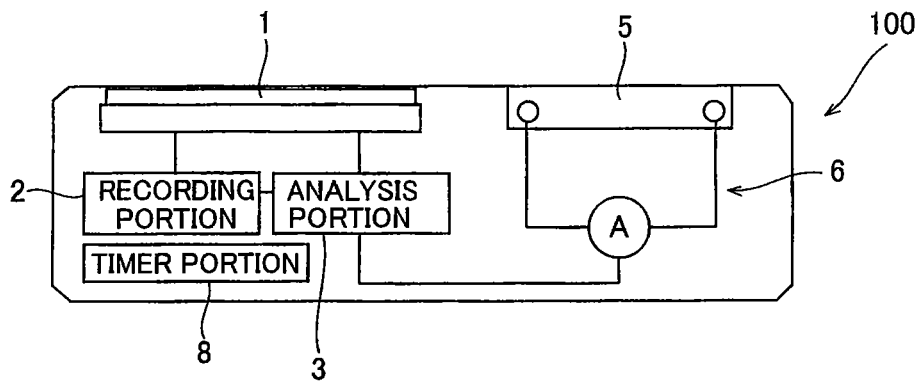
FIG. 3 is a schematic side view showing the measurement apparatus used in the blood glucose AUC measurement method according to the first embodiment shown in FIG. 1.

As shown in FIGS. 1 to 3, a measurement apparatus 100 comprises a display portion 1, a recording portion 2, an analysis portion 3, a power supply 4, an installation portion 5 for installing a sensor chip 200 and a gel 301 of a collection member 300 (see FIG. 6) described later, an electric circuit 6 connected to the sensor chip 200 installed in the installation portion 5, operation buttons 7 for a user (subject) to operate the measurement apparatus 100, and a timer portion 8.

The display portion 1 has a function of displaying a measurement result by the analysis portion 3, data recorded in the recording portion 2 and so on. The recording portion 2 is provided for storing past data. The analysis portion 3 has a function of calculating a glucose concentration and an electrolyte (NaCl) concentration based on an output value of the electric circuit 6. The installation portion 5 has a concave shape and is configured to be capable of storing the sensor chip 200 and the gel 301 of the collection member 300. The electric circuit 6 includes a glucose measurement circuit 6a and an electrolyte measurement circuit 6b. The glucose measurement circuit 6a includes terminals 6c and 6d which are exposed in the installation portion 5, and the electrolyte measurement circuit 6b includes terminals 6e and 6f which are exposed in the installation portion 5. The electric circuit 6 includes a switch 6g for switching the glucose measurement circuit 6a and the electrolyte measurement circuit 6b. The user can switch the glucose measurement circuit 6a and the electrolyte measurement circuit 6b by operating the operation buttons 7 to operate the switch 6g. The operation buttons 7 are provided for switching the switch 6g, switching display on the display portion 1, setting the timer portion 8 and so on. The timer portion 8 has a function of informing the user of extraction end time for terminating extraction in a prescribed time from the start of glucose extraction, and has an alarm device (not shown) built-in for that purpose.

[Structure of Sensor Chip]

The sensor chip 200 includes a plastic substrate 201, a pair of glucose measurement electrodes 202 provided on an upper surface of the substrate 201, and a pair of electrolyte measurement electrodes 203 provided on the upper surface of the substrate 201. The glucose measurement electrode 202 is constituted by a work electrode 202a with a GOD enzyme membrane (GOD: glucose oxidase) formed on a platinum electrode and a counter electrode 202b formed of a platinum electrode, and the electrolyte measurement electrode 203 is constituted by a work electrode 203a made of silver/silver chloride and a counter electrode 203b made of silver/silver chloride. The work electrode 202a and the counter electrode 202b of the glucose measurement electrode 202 are configured to be in contact with the terminals 6c and 6d of the glucose measurement circuit 6a, respectively in a state where the sensor chip 200 is installed in the installation portion 5 of the measurement apparatus 100. Similarly, the work electrode 203a and the counter electrode 203b of the electrolyte measurement electrode 203 are configured to be in contact with the terminals 6e and 6f of the electrolyte measurement circuit 6b, respectively in a state where the sensor chip 200 is installed in the installation portion 5 of the measurement system 100.

[Structure of Collection Member]

The collection member 300 has a structure in which the gel 301 having hygroscopicity and nonconductivity (substantially electrolyte-free nature) capable of retaining tissue fluid oozing from the body of the subject to the skin by passive diffusion is supported by a support member 302. The gel 301 is made of polyvinyl alcohol. The support member 302 has a concave portion 302a and a flange portion 302b formed on an outer periphery of the concave portion 302a, and the gel 301 is held in the concave portion 302a. An adhesive layer 303 is provided on a surface of the flange portion 302b, and a peel-off paper 304 for sealing the gel 301 held in the concave portion 302a is applied by the adhesive layer 303 in a pre-measurement state. During measurement, the peel-off paper 304 is peeled off, whereby the gel 301 and the adhesive layer 303 are exposed, and the gel 301 can be applied and fixed to the skin of the subject through the adhesive layer 303 in a state where the gel 301 is in contact with the skin of the subject.

The gel 301 is configured to be capable of accumulating the aforementioned measurement target component in the tissue fluid extracted from an organism for at least 60 minutes. More specifically, the gel 301 has a sufficient volume to allow accumulation of the aforementioned measurement target component in the tissue fluid extracted from the organism for at least 60 minutes. The volume of this gel 301 is determined depending on a tissue-fluid extraction time. More specifically, if the extraction time is 60 minutes, the volume of the gel is preferably at least 33 μL. If the extraction time is 120 minutes, the volume of the gel is preferably at least 66 μL, and if the extraction time is 180 minutes, the volume of the gel is preferably at least 100 μL. The volume of the gel capable of accumulating the measurement target component can be obtained by a method described later.

[Structure of Puncture Device]

Figure 7:
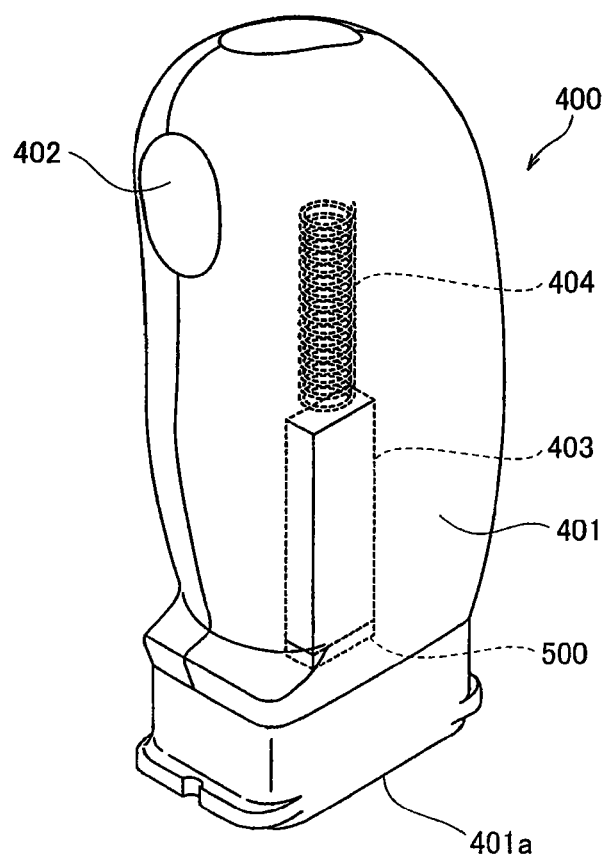
FIG. 7 is a perspective view showing a puncture device used in the blood glucose AUC measurement method according to the first embodiment of the present invention.
Figure 8:
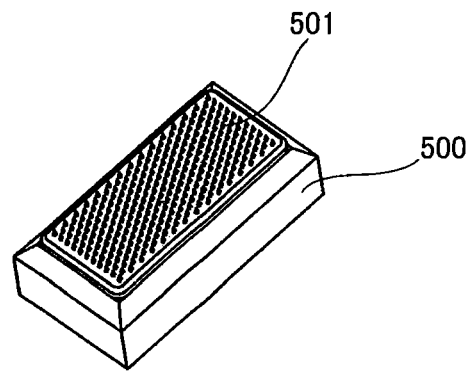
FIG. 8 is a perspective view showing a fine needle chip mounted on the puncture device used in the blood glucose AUC measurement method according to the first embodiment shown in FIG. 7.
Figure 9:
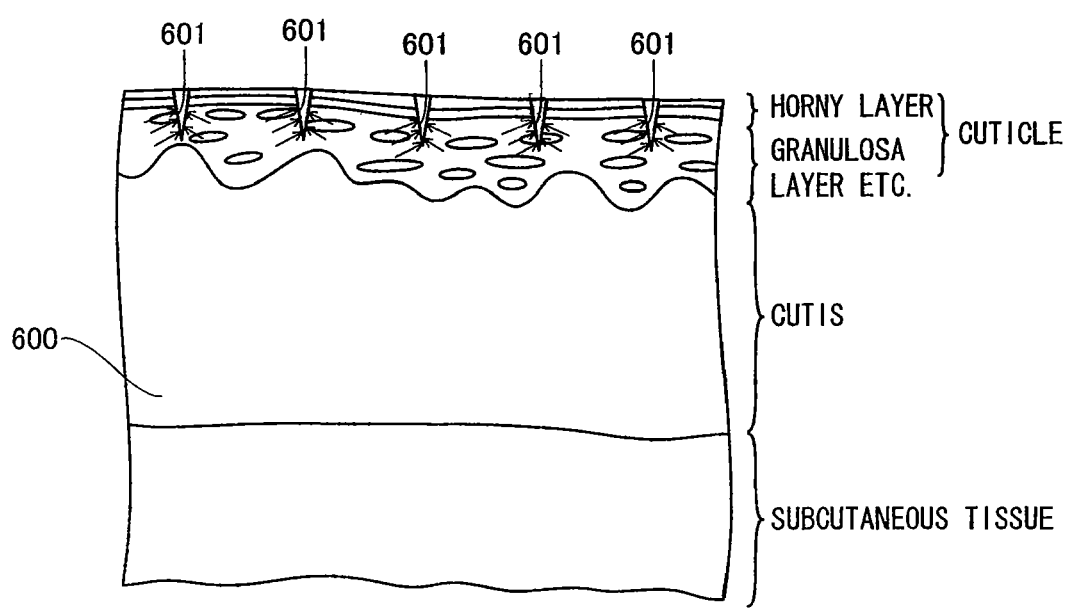
FIG. 9 is a sectional view showing the skin having fine pores formed thereon.

As shown in FIGS. 7 to 9, a puncture device 400 is a device which is mounted with a fine needle chip 500 sterilized and forms fine pores (fine pores 601) for extracting the tissue fluid on the skin 600 of the subject by bringing fine needles 501 of the fine needle chip 500 into contact with the cuticle of the organism, specifically the skin 600 of the subject. In a case where the fine pores 601 are formed by the puncture device 400, each of the fine needles 501 of the fine needle chip 500 has such a depth that the fine pores 601 penetrate through the cuticle of the skin 600 but not reach a deep portion of the cutis. As shown in FIG. 7, the puncture device 400 comprises a housing 401, a release button 402 provided on a surface of the housing 401, and an array chuck 403 and a spring member 404 which are provided inside the housing 401. An opening (not shown) is formed on a bottom portion 401a of the housing 401. The spring member 404 has a function of urging the array chuck 403 downward. The array chuck 403 is capable of being mounted with the fine needle chip 500 on a lower end thereof. A plurality of the fine needles 501 are formed on a lower surface of the fine needle chip 500. Further, the puncture device 400 has a fixing mechanism (not shown) for fixing the array chuck 403 in a state where the array chuck 403 is pushed upward against the urging force of the spring member 404, and the user (subject) presses down the release button 402 to release fixation of the array chuck 403 by the fixing mechanism so that the array chuck 403 projects downward due to the urging force of the spring member 404 and the fine needle chip 500 hits the skin.

[Blood Glucose AUC Measurement Method]

Next, a measurement procedure of a blood glucose AUC measurement method according to the first embodiment of the present invention is described with reference to FIGS. 6 to 13.

Figure 10:
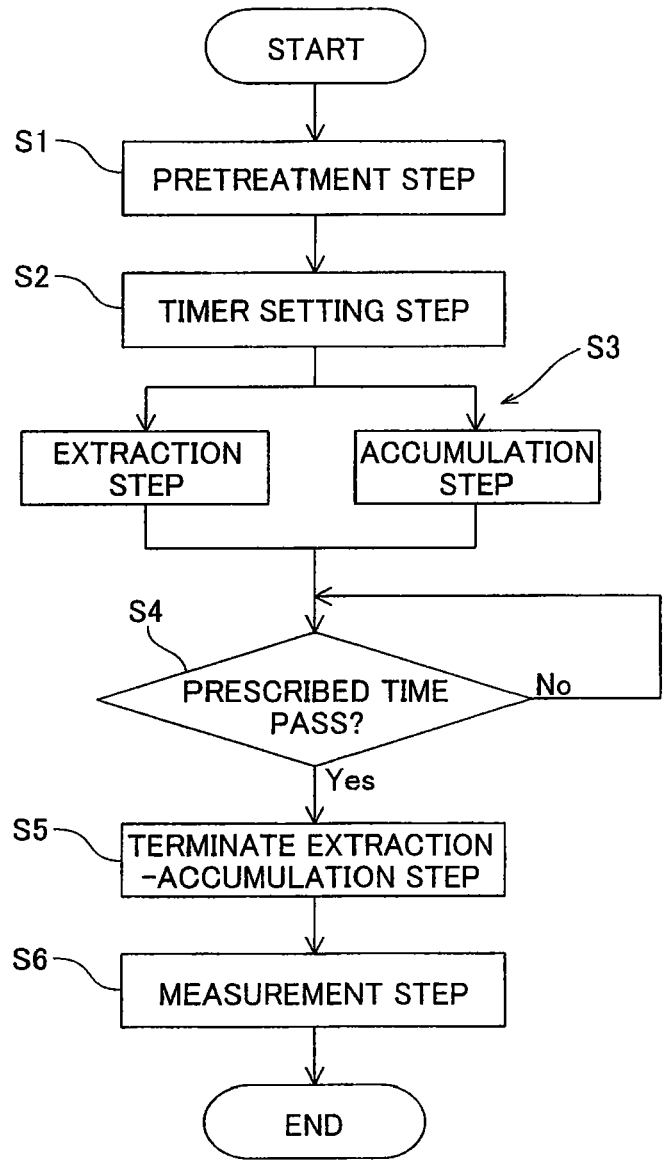
FIG. 10 is a flow chart for illustrating a measurement procedure of the blood glucose AUC measurement method according to the first embodiment of the present invention.

First, an outline of the measurement procedure of the blood glucose AUC measurement method according to the present invention is described with reference to FIG. 10. Among steps shown in FIG. 10, steps S1 to S5 are carried out by those practicing the measurement, and a step S6 is carried out by the measurement apparatus 100 according to the first embodiment.

First, a site to be measured of the subject is cleaned and fine pores are formed in the site to be measured using the puncture device 400 (step S1). Next, a tissue-fluid extraction time is set using the timer portion 8 provided in the measurement apparatus 100 (step S2). Next, the collection member 300 is mounted on the site to be measured, and the tissue fluid extraction and the accumulation of a component in the tissue fluid start (step S3). Then, it is determined whether or not an end of the extraction time set at the step S2 is informed by an alarm of the timer portion 8 (step S4), and in a case where it is informed, the collection member 300 is removed and the tissue fluid extraction is terminated (step S5). Next, the collection member 300 terminating the extraction is installed in the installation portion 5 of the measurement apparatus 100, glucose measurement and blood glucose AUC analysis are carried out (step S6), and measurement is terminated.

Hereinafter, respective steps are described in detail.

(Step S1: Pretreatment Step)

First, the subject cleans the skin 600 with alcohol or the like for removing substances (sweat, dust, etc.) becoming a disturbing factor for measurement results. After the cleaning, the fine pores 601 are formed on the skin 600 with the puncture device 400 (see FIG. 7) mounted with the fine needle chip 500. Specifically, the release button 402 is pressed down in a state where the opening (not shown) of the bottom portion 401a of the puncture device 400 is disposed on the site to be measured. Thus, the fixation of the array chuck 403 by the fixing mechanism (not shown) is released, and the array chuck 403 moves to the skin 600 due to the urging force of the spring member 404. Subsequently, the fine needles 501 of the fine needle chip 500 (see FIG. 8) mounted on the lower end of the array chuck 403 come into contact with the skin 600 of the subject at a prescribed speed. Thus, the fine pores 601 are formed on the skin 600 of the subject, as shown in FIG. 9.

(Step S2: Timer Setting Step)

Next, the subject sets time of the timer portion 8 of the measurement apparatus 100 by operating the operation buttons 7. The set time can be set at an arbitrary time so far as it is at least 60 minutes. The following respective steps are described with an example of setting the set time at 180 minutes.

(Steps S3 to S5: Extraction-Accumulation Steps)

Figure 11:
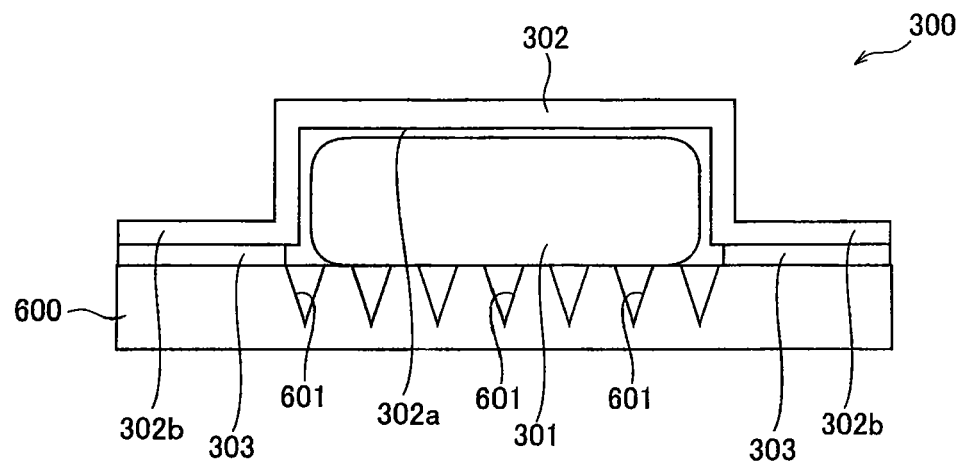
FIG. 11 is a diagram for illustrating the measurement procedure of the blood glucose AUC measurement method according to the first embodiment of the present invention.

Next, as shown in FIG. 11, the subject removes the peel-off paper 304 (see FIG. 6) of the collection member 300 and applies the collection member 300 to the skin such that the gel 301 is arranged on the site where the fine pores 601 are formed (step S3). Thus, the site where the fine pores 601 are formed and the gel 301 are in contact with each other, the tissue fluid containing glucose and an electrolyte (NaCl) starts to move to the gel 301 through the fine pores 601, and the extraction starts. At the start of the extraction, the subject turns on the timer portion 8 of the measurement apparatus 100. Subsequently, a state where the collection member 300 is applied to the skin 600 is kept until the prescribed time (set time of the alarm) passes (step S4). Then, the subject removes the collection member 300 from the skin 600 when the alarm sounds after a lapse of the prescribed time (step S5). Here, since the alarm of the timer portion 8 is set at 180 minutes, the tissue fluid is continuously extracted from the skin for 180 minutes. Thus, the extraction-accumulation step is terminated.

(Step S6: Measurement Step)

Figure 12:
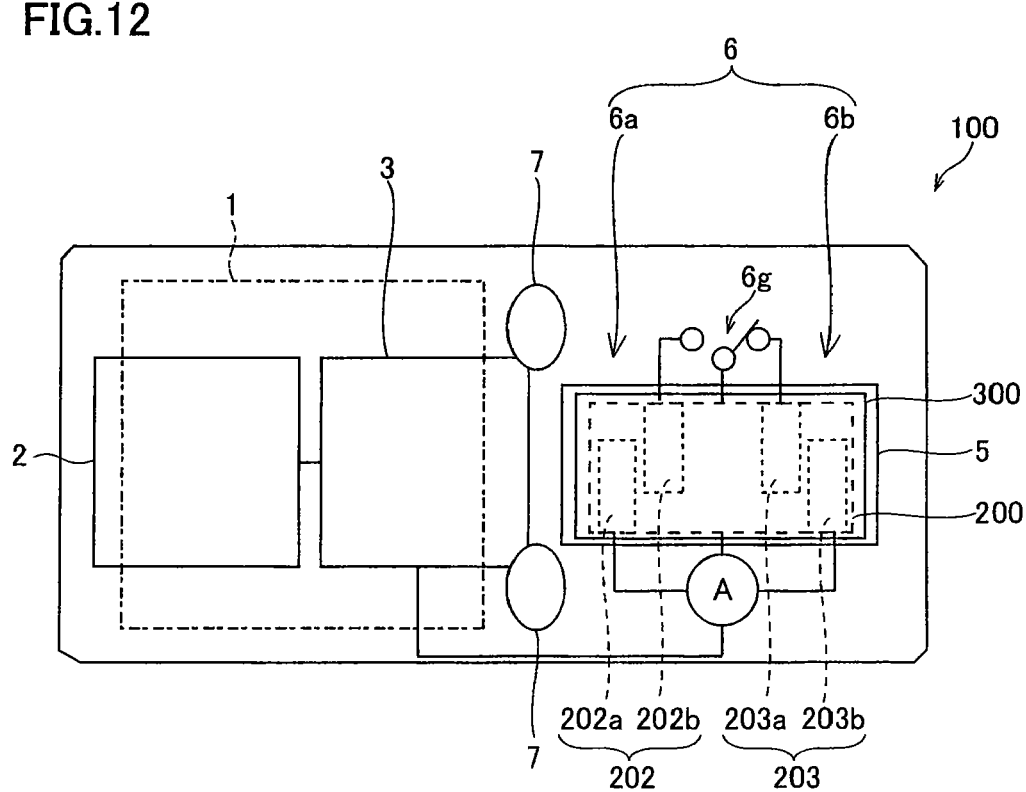
FIG. 12 is a diagram for illustrating the measurement procedure of the blood glucose AUC measurement method according to the first embodiment of the present invention.
Figure 13:
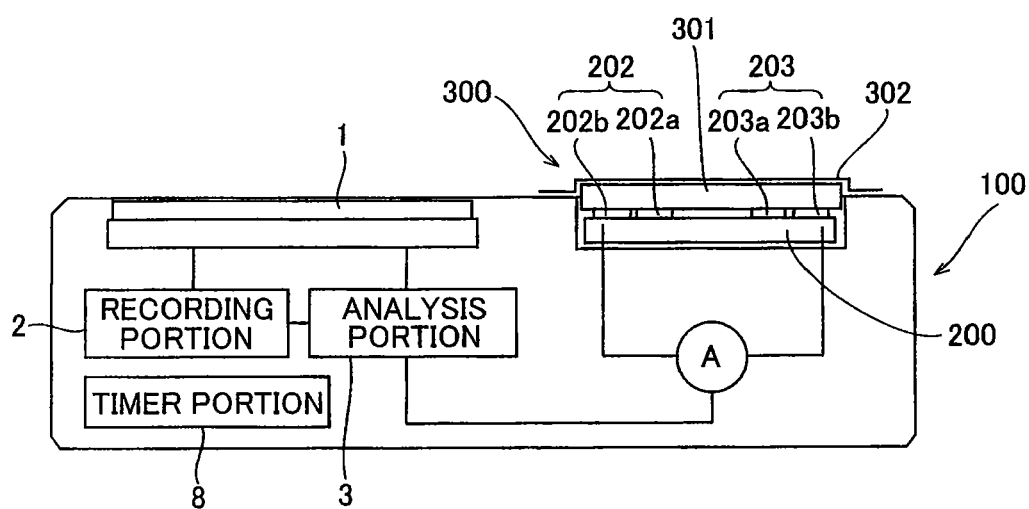
FIG. 13 is a diagram for illustrating the measurement procedure of the blood glucose AUC measurement method according to the first embodiment of the present invention.

Next, as shown in FIGS. 12 and 13, the subject installs the sensor chip 200 in the installation portion 5 of the measurement apparatus 100 and places the gel 301 of the collection member 300 on the sensor chip 200. Thus, a first circuit is constituted by the glucose measurement circuit 6a of the measurement apparatus 100, the glucose measurement electrode 202 of the sensor chip 200 and the gel 301 of the collection member 300, and a second circuit is constituted by the electrolyte measurement circuit 6b of the measurement apparatus 100, the electrolyte measurement electrode 203 of the sensor chip 200, and the gel 301 of the collection member 300.

In a case where an extracted glucose concentration is measured, the subject switches the switch 6g to the glucose measurement circuit 6a by the operation buttons 7 and instructs start of measurement. Thus, a constant voltage is applied to the first circuit, and a current value I(glc) detected by an ammeter is input into the analysis portion 3. Here, the following formula (1) is established between the current value I(glc) and the glucose concentration C(glc) of the gel 301:

$$C(glc) = A \times I(glc) + B \quad (A \text{ and } B \text{ are constant numbers}) \qquad (1)$$

The analysis portion 3 calculates the glucose concentration C(glc) from the current value I(glc) based on the aforementioned formula (1).

Further, the analysis portion 3 calculates the extraction glucose quantity M(glc) using the obtained glucose concentration C(glc) and the extraction solvent quantity, or a volume V of the gel, based on the following formula (2):

$$M(glc) = C(glc) \times V \qquad (2)$$

Further, in a case where an extracted electrolyte concentration is measured, the subject switches the switch 6g to the electrolyte measurement circuit 6b by the operation buttons 7 and instructs start of measurement. Thus, a constant voltage is applied to the second circuit, and a current value I(ele) detected by the ammeter is input into the analysis portion 3. Here, the following formula (3) is established between the current value I(ele) and the electrolyte concentration C(NaCl) of the gel 301:

$$C(NaCl) = C \times I(ele) + D \quad (C \text{ and } D \text{ are constant numbers}) \qquad (3)$$

The analysis portion 3 calculates the electrolyte concentration C(NaCl) from the current value I(ele) based on the aforementioned formula (2).

Further, the analysis portion 3 calculates an electrolyte extraction rate J at the extraction site from the electrolyte concentration C(NaCl), the volume V of the gel 301, and an extraction time t based on the following formula (4):

$$J = C(NaCl) \times V \times 1/t \quad (4)$$

Then, the analysis portion 3 calculates a glucose permeability P(glc) indicative of the ease of extracting glucose from the calculated electrolyte extraction rate J based on the following formula (5):

$$P(glc) = E \times J + F \text{ ($E$ and $F$ are constant numbers)} \quad (5)$$

The formula (5) is obtained as follows. The glucose permeability P(glc) indicative of the ease of extracting glucose is normally given by a ratio (this ratio is tentatively referred to as a true glucose permeability P'(glc)) of the blood glucose AUC obtained by blood drawing to the quantity of extracted glucose. As described later, because the true glucose permeability P'(glc) indicates a constant correlation with the electrolyte extraction rate J, the aforementioned formula (5) can be obtained by obtaining an approximation formula based on the electrolyte extraction rate J and the true glucose permeability P'(glc).

According to the aforementioned formula (5), it is possible to obtain the glucose permeability P(glc) indicative of the ease of extracting glucose based on the electrolyte extraction rate J obtainable without conducting the blood drawing.

The analysis portion 3 calculates a predicted blood glucose AUC (predicted AUC) from the extraction glucose quantity M(glc) obtained by the formula (2) and the glucose permeability P(glc) obtained by the formula (5) based on the following formula (6):

$$\text{predicted } AUC = M(glc)/P(glc) \quad (6)$$

This predicted blood glucose AUC (predicted AUC) is a value having a high correlation with a blood drawing blood glucose AUC calculated by plural times of blood drawing. Correlativity between the predicted blood glucose AUC and the blood drawing blood glucose AUC is described later in detail. A value of this predicted blood glucose AUC is displayed on the display portion 1 and recorded in the recording portion 2. Thus, the measurement step is terminated.

Modification of First Embodiment

In the first embodiment, the structure of calculating the glucose concentration C(glc), the glucose quantity M(glc), the electrolyte concentration C(NaCl), the electrolyte extraction rate J, and the glucose permeability P(glc) in the analysis portion 3 to measure the predicted AUC is exemplified, but this structure may not be used. For example, the formula (6) for calculating the predicted AUC can be replaced with the following formula by the formulas (1) to (5):

$$\text{predicted } AUC = \{(A \times I(glc) + B) \times t\}/[E \times (C \times I(ele) + D) \times F] \text{ ($A$ to $F$ are constant numbers)}$$

Therefore, if the aforementioned formula is used, it is possible that the analysis portion 3 directly calculates the predicted AUC based on the current value I(glc) and the current value I(ele).

Second Embodiment

Figure 14:
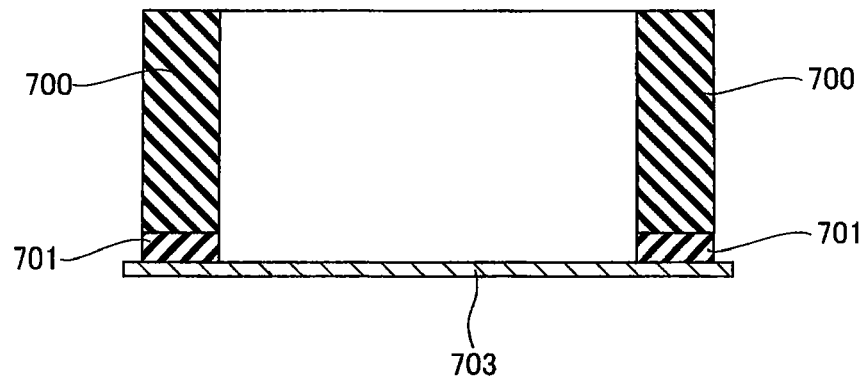
FIG. 14 is an explanatory sectional view showing a collection member used in a blood glucose AUC measurement method according to a second embodiment of the present invention.

Next, a blood glucose AUC measurement method according to a second embodiment of the present invention is described with reference to FIGS. 14 and 15. According to this second embodiment, pure water is used as an extraction medium instead of a gel. Because a measurement procedure of the second embodiment is the same as that of the first embodiment at the step S1 and the step S2, the second embodiment is described according to the measurement flow shown in the first embodiment without the steps S1 and S2.

(Steps S3 to S5: Extraction-Accumulation Steps)

Figure 4:
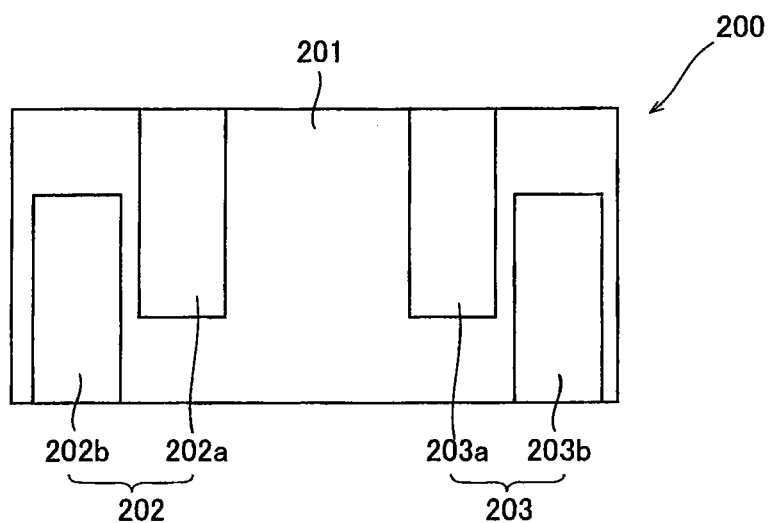
FIG. 4 is a schematic plan view showing the sensor chip used in the blood glucose AUC measurement method according to the first embodiment shown in FIG. 1.
Figure 5:
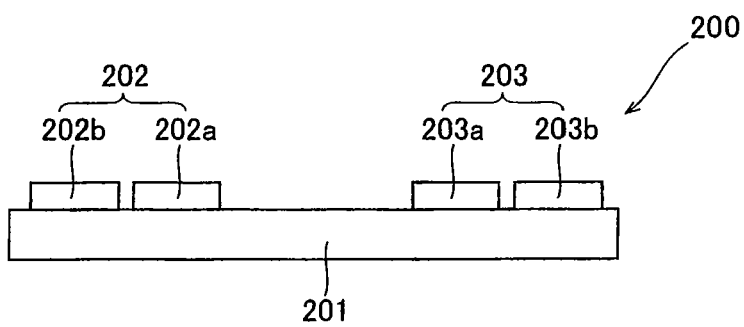
FIG. 5 is a schematic side view showing the sensor chip used in the blood glucose AUC measurement method according to the first embodiment shown in FIG. 1.

As shown in FIG. 4, tissue fluid is extracted using a cylindrical support member 700 having upper and lower openings. As shown in FIG. 15, a subject applies the support member 700 to the skin 600 with an adhesive layer 701 such that a hollow portion of the support member 700 is arranged on a site where fine pores 601 are formed. After a prescribed quantity of pure water 704 is injected with a pipette into the support member 700 through the upper opening, the upper opening of the support member 700 is sealed by a seal member 702 for preventing evaporation of the pure water 704. Thus, the site where the fine pores 601 are formed and the pure water 704 are in contact with each other, the tissue fluid containing glucose and an electrolyte (NaCl) starts to move into the pure water 704 through the fine pores 601, and the extraction starts (step S3). At the start of the extraction, the subject turns on an alarm device. Subsequently, a state where the support member 700 is applied to the skin 600 is kept until a prescribed time (set time of the alarm) passes (step S4). Then, the subject removes the seal member 702 when the alarm sounds after a lapse of the prescribed time and collects fluid in the support member 700 with the pipette (step S5). Thus, the extraction-accumulation step is terminated.

(Step S6: Measurement Step)

Next, a conductivity G of the collected fluid is measured. Since most of the electrolyte in the fluid after extraction is sodium chloride, it is possible to obtain an electrolyte concentration C(NaCl) by measuring the conductivity G of the fluid. A correlation between the conductivity and the electrolyte concentration is described later.

A glucose permeability P(glc) is calculated with the calculated electrolyte concentration C(NaCl) and the aforementioned formulas (4) and (5).

Next, a glucose concentration C(glc) is measured by putting the fluid after extraction in a high-performance liquid chromatography. The extraction glucose quantity M(glc) is calculated from this glucose concentration C(glc) and a volume V of the used pure water 704 based on the aforementioned formula (2). Then, a predicted blood glucose AUC is calculated from the obtained extraction glucose quantity M and the glucose permeability P(glc) based on the aforementioned formula (6). Thus, the measurement step is terminated.

Third Embodiment

Figure 6:
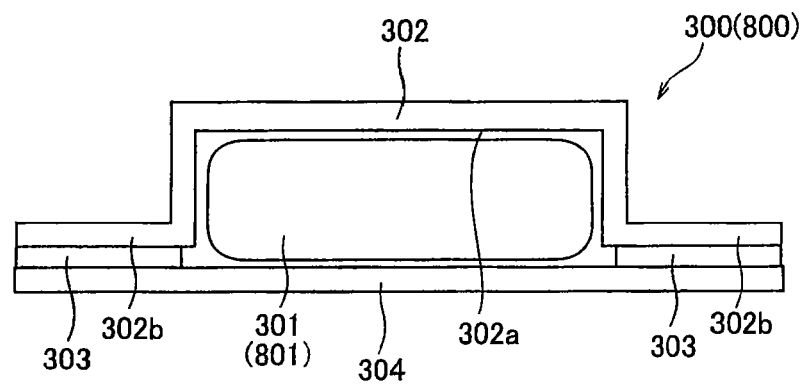
FIG. 6 is a schematic sectional view showing a collection member used in a blood glucose AUC measurement method according to each of first and third embodiments of the present invention.

A collection member used in a blood glucose AUC measurement method according to a third embodiment of the present invention is described with reference to FIG. 6.

In each of the first and second embodiments, a mode in which a gel containing pure water or pure water is used as an extraction medium has been described. According to the third embodiment, tissue fluid is extracted using a gel containing a hypertonic aqueous solution having a high osmotic pressure instead of this pure water. Because a measurement procedure of the third embodiment is the same as that of the first embodiment, a description of the measurement procedure is omitted.

A collection member 800 according to the third embodiment has a structure in which a gel 801 having hygroscopicity (substantially $Na^+$-free nature) capable of retaining tissue fluid extracted from the skin of a subject is supported by a support member 302. The gel 801 of this embodiment is made of polyvinyl alcohol. This gel 801 contains a hypertonic aqueous solution having a higher osmotic pressure than pure water. This hypertonic aqueous solution is an aqueous solution containing an auxiliary component other than a measurement target component, contained with the measurement target component such as glucose in the tissue fluid. According to the third embodiment, at least one selected from a group consisting of kalium chloride, glycine and urea is used as the auxiliary component contained with the measurement target component such as glucose in the tissue fluid. A concentration of this auxiliary component is 0.2 mM (mmol/L) or more.

The remaining structure of the third embodiment is similar to that of the aforementioned first embodiment.

Fourth Embodiment

Next, a blood glucose AUC measurement method according to a fourth embodiment of the present invention is described with reference to FIG. 15. According to the fourth embodiment, tissue fluid is extracted using a hypertonic aqueous solution. Because a measurement procedure of the fourth embodiment is the same as that of the aforementioned second embodiment, descriptions of steps other than extraction-accumulation steps at steps S3 to S5 are omitted.

(Steps S3 to S5: Extraction-Accumulation Steps)

Figure 15:
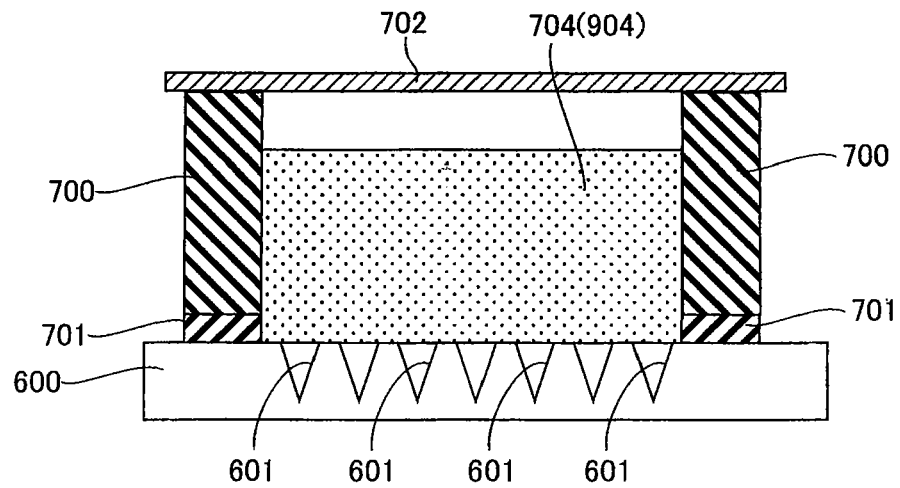
FIG. 15 is a diagram for illustrating a measurement procedure of a blood glucose AUC measurement method according to each of second and fourth embodiments of the present invention.

According to the fourth embodiment, as shown in FIG. 15, a subject removes a peel-off paper 703 and applies a support member 700 to a site where fine pores 601 are formed with an adhesive layer 701. Then, a prescribed amount of a hypertonic aqueous solution 904 (KCl aqueous solution) containing kalium chloride (KCl) as an auxiliary component is injected with a pipette (not shown) into the support member 700 through an upper opening. Thereafter, the upper opening of the support member 700 is sealed by a seal member 702 for preventing evaporation of this KCl aqueous solution 904. Thus, the site where the fine pores 601 are formed and the hypertonic aqueous solution 904 (KCl aqueous solution) are in contact with each other, tissue fluid containing glucose and an electrolyte (NaCl) starts to move into the KCl aqueous solution 904 through the fine pores 601, and the extraction starts (step S3). At the start of the extraction, the subject turns on an alarm device of a timer portion 8. Subsequently, a state where the support member 700 is applied to the skin 600 is kept until a prescribed time (set time of the alarm) passes (step S4). Then, the subject removes the seal member 702 when the alarm sounds after a lapse of the prescribed time and collects fluid (hypertonic aqueous solution 904 including the extracted tissue fluid) in the support member 700 with the pipette (step S5). Thus, the extraction-accumulation step is terminated.

Fifth Embodiment

In each of the measurement methods according to the first and third embodiments, the gel 301 (801) in which the tissue fluid extracted from the body is accumulated is set on the installation portion 5 of the measurement apparatus 100 and the glucose concentration and so on in this gel 301 (801) are measured, but a specimen in the gel 301 (801) is collected in the pure water in a special container, and a specimen concentration in this collection solution can be also measured.

Figure 16:
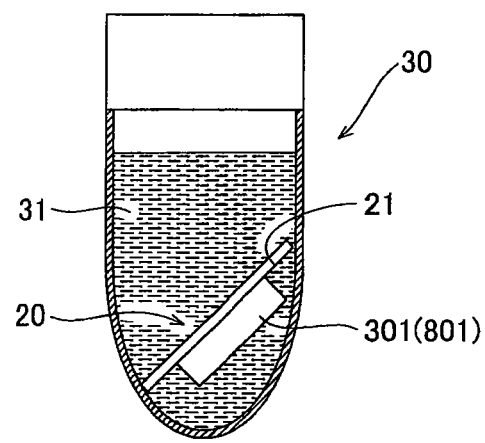
FIG. 16 is a diagram illustrating an example of a method of collecting a specimen from a gel used in a blood glucose AUC measurement method according to a fifth embodiment of the present invention.
Figure 17:
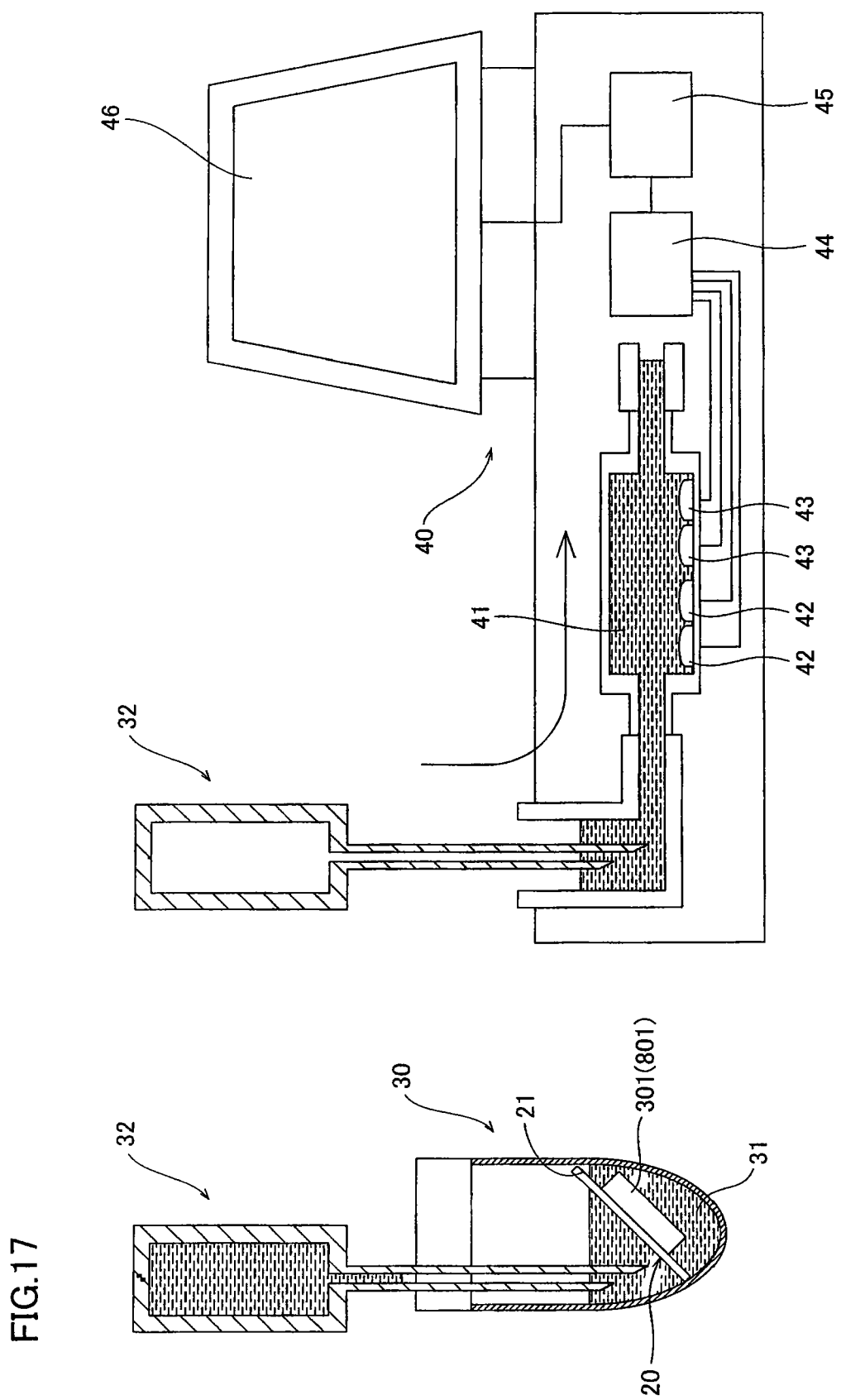
FIG. 17 is a diagram illustrating the example of the method of collecting the specimen from the gel used in the blood glucose AUC measurement method according to the fifth embodiment of the present invention.

For example, as shown in FIG. 16, a gel reservoir 20 (in which the gel 301 (801) is disposed on one surface of a substrate 21) comprising the gel 301 (801) which has finished extraction of a specimen from the skin is immersed in a collection fluid 31 made of pure water in a collection tube 30, whereby the specimen accumulated in the gel 301 (801) is collected. After collection of the specimen is terminated, the collection fluid 31 in the collection tube 30 is moved to a measurement portion 41 of a measurement apparatus 40 through a syringe 32, as shown in FIG. 17. The measurement portion 41 is provided with glucose concentration measurement electrodes 42 and sodium ion concentration measurement electrodes 43 which are similar to those of the aforementioned measurement apparatus 100. A glucose concentration and a sodium ion concentration are measured by an electric control portion 44 and an analysis portion 45 by the aforementioned method using the formulas (1) to (6), and blood glucose AUC is analyzed. The obtained result is output on a display portion 46.

Figure 18:
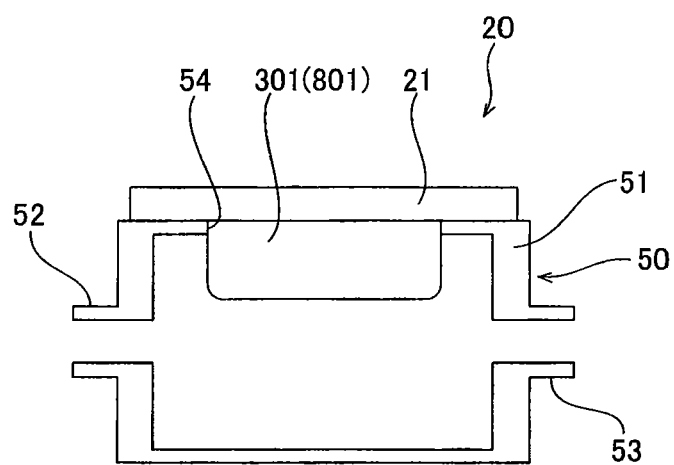
FIG. 18 is a diagram illustrating another example of a method of collecting the specimen from the gel used in the blood glucose AUC measurement method according to the fifth embodiment of the present invention.

Further, the specimen in the gel 301 (801) can be also collected by another method. As shown in FIG. 18, the gel reservoir 20 comprising the gel 301 (801) which has finished extraction of the specimen from the skin is set on a special collection cartridge 50. This collection cartridge 50 is formed of a cartridge main body 51 in a box shape. An inlet 52 of the collection fluid is formed on one of wall surfaces of the cartridge main body 51 which are opposed to each other, and an outlet 53 of the collection fluid is formed on the other. The gel reservoir 20 is so set on the collection cartridge 50 that the gel 301 (801) protrudes into this cartridge main body 51 from an opening 54 formed on one surface of the cartridge main body 51.

Figure 19:
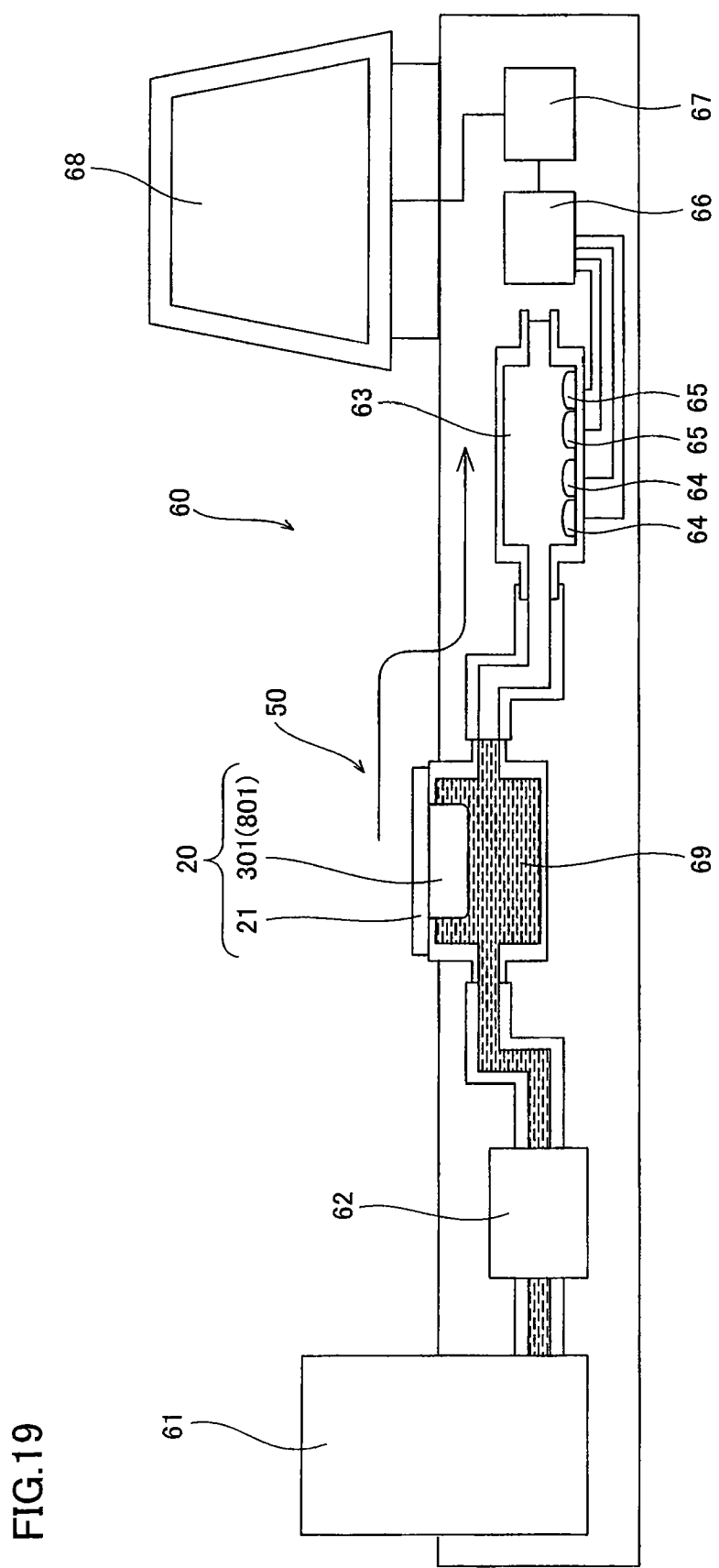
FIG. 19 is a diagram illustrating another example of the method of collecting the specimen from the gel used in the blood glucose AUC measurement method according to the fifth embodiment of the present invention.

Next, as shown in FIG. 19, the collection cartridge 50 is set on a prescribed place of a measurement apparatus 60. This measurement apparatus 60 comprises a tank portion 61 and a pump portion 62, and a flow passage for the collection fluid is formed to a measurement portion 63 through the tank portion 61, the pump portion 62 and the cartridge main body 51. Further, the measurement portion 63 is provided with glucose concentration measurement electrodes 64 and sodium ion concentration measurement electrodes 65 which are similar to those of the aforementioned measurement apparatus 100. After the collection cartridge 50 is set on the measurement apparatus 60, a collection fluid 69 stored in the tank portion 61 for collecting the specimen is transferred into the cartridge main body 51 by driving the pump portion 62 (see FIG. 19). Although illustration is omitted, a valve is arranged on a downstream side of the outlet 53 of the cartridge main body 51, and this valve is closed before the collection fluid 69 is transferred into the cartridge main body 51.

Figure 20:
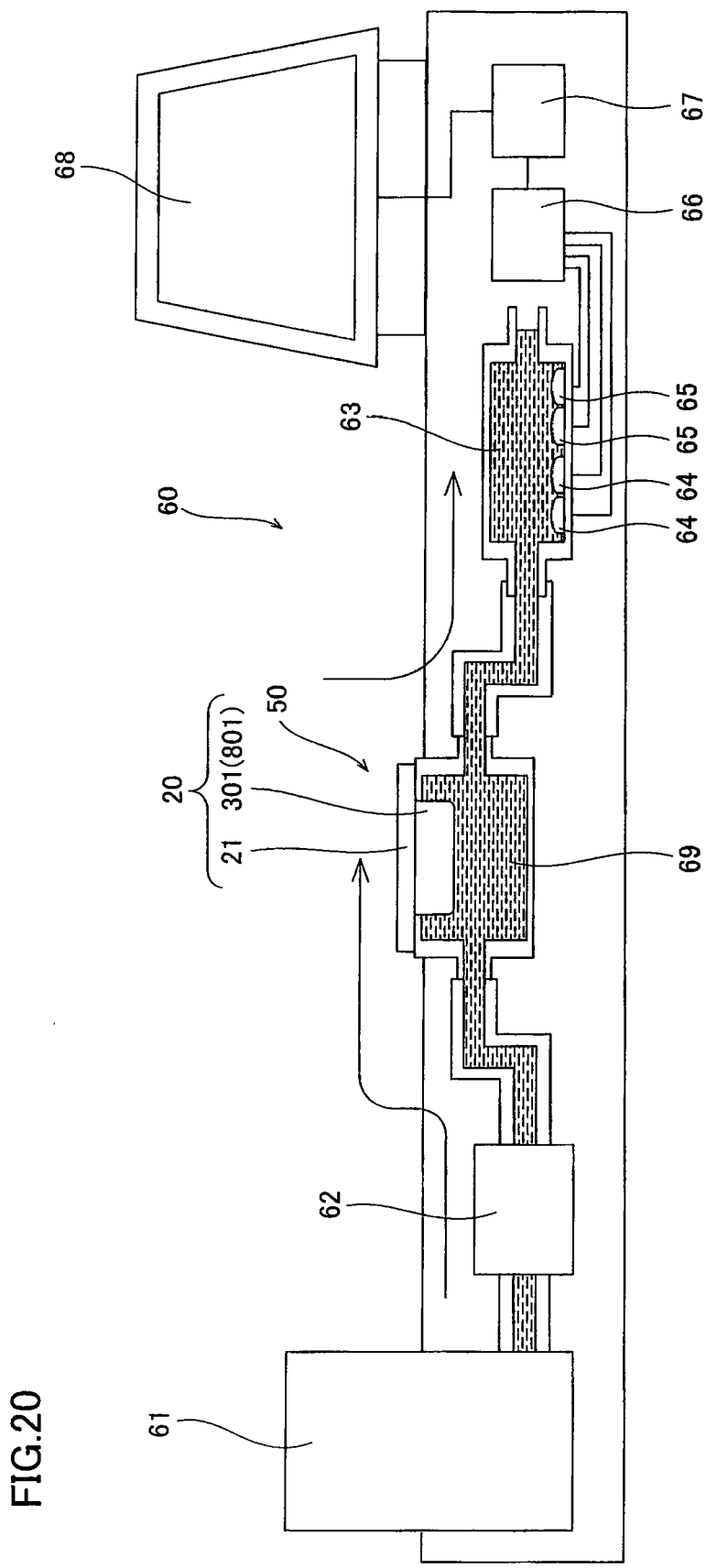
FIG. 20 is a diagram illustrating another example of the method of collecting the specimen from the gel used in the blood glucose AUC measurement method according to the fifth embodiment of the present invention.

While a state where the cartridge main body 51 is filled up with the collection fluid 69 is kept for a given length of time, the specimen in the gel 301 (801) is collected in the collection fluid 69. Subsequently, the aforementioned valve on the downstream side of the outlet 53 is opened, and the collection fluid 69 is transferred to the measurement portion 63 by driving the pump portion 62, as shown in FIG. 20. Next, a glucose concentration and a sodium ion concentration are measured by an electric control portion 66 and an analysis portion 67 by the aforementioned method using the formulas (1) to (6), and blood glucose AUC is analyzed. The obtained result is output on a display portion 68.

[Principle of Blood Glucose AUC Measurement Method]

Next, the measurement principle of the blood glucose AUC measurement method is described with reference to FIGS. 21 and 22.

It is known that a glucose concentration in the tissue fluid (IG(t)) changes depending on a glucose concentration in blood (BG(t)) and the glucose concentration in the tissue fluid (IG(t)) and the glucose concentration in blood (BG(t)) have a strong correlation with each other in general. The glucose concentration in the tissue fluid (IG(t)) can be expressed as the following formula (7) using a constant number α.

$$BG(t) = \alpha \times IG(t) \qquad (7)$$

Figure 21:
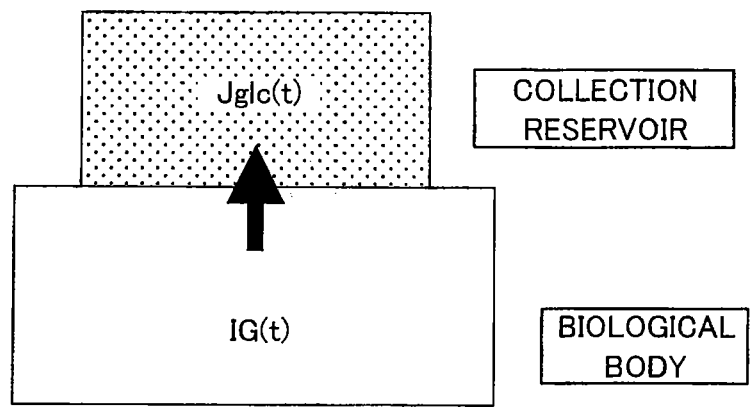
FIG. 21 is a schematic view for illustrating the measurement principle of the blood glucose AUC measurement method according to each of the first and second embodiments of the present invention.

As shown in FIG. 21, consider a case of fitting an extraction medium, which is fluid or a gel, on an organism and collecting tissue fluid from the organism through the skin. Let a glucose extraction rate J(glc) be defined as the quantity of glucose extracted from the skin to the extraction medium per unit time, J(glc)(t) be defined as a glucose extraction rate at a given time t, and IG(t) be defined as a glucose concentration in the tissue fluid at the time t. At this time, the glucose extraction rate J(glc)(t) is expressed as a product of the glucose concentration IG(t) and a glucose permeability P(glc) by the following formula (8):

$$J(glc)(t) = P(glc) \times IG(t) \qquad (8)$$

The glucose permeability P(glc) is a coefficient representing permeability of glucose with respect to the skin, and the quantity of glucose extracted from the skin per unit time is increased as the glucose permeability P(glc) is increased.

Here, consider a case of performing an extraction only for a prescribed time T. On the left side of the aforementioned formula (8), when integrating J(glc)(t) across the extraction time T, the integrated value becomes the total quantity M(glc)(T) of glucose extracted from the organism to the extraction medium within the extraction time T. This relationship is shown in the following formula (9):

$$M(glc)(T) = \int J(glc)(t) \qquad (9)$$

For example, if the glucose extraction rate J(glc)(t)=10 ng/min, the total quantity M(glc) of glucose extracted to the reservoir in a case where the extraction time T is 60 min is M(glc)=10 ng/min×60 min=600 ng.

Figure 22:
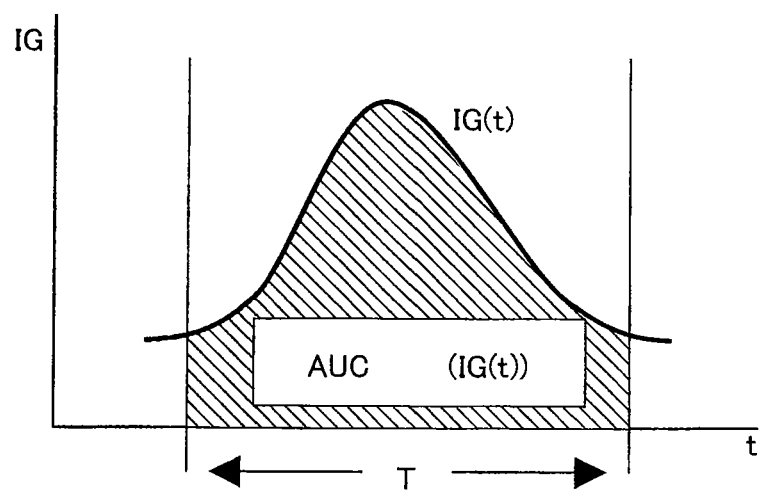
FIG. 22 is a schematic view for illustrating the measurement principle of the blood glucose AUC measurement method according to each of the first and second embodiments of the present invention.

On the other hand, n the right side of the aforementioned formula (8), when integrating the glucose concentration IG(t) in the tissue fluid across the time t, the value becomes the value becomes the area (area under the curve AUC (IG(t))) of the figure (hatched area) defined by the graph of the glucose concentration IG(t) during the time T, as show in FIG. 22. This relationship is shown in the following formula (10):

$$AUC(IG(t)) = \int IG(t) \qquad (10)$$

As expressed by the aforementioned formula (7), there is a correlation between IG(t) and BG(t), and hence there is also a correlation between the area under the curve AUC(IG(t)) and an area under the curve AUC(BG(t)). Therefore, a relation between the area under the curve AUC(BG(t)) and the area under the curve AUC(IG(t)) is expressed by the following formula (11) with a constant number a:

$$AUC(BG(t)) = a \times AUC(IG(t)) \qquad (11)$$

In a case of considering an integral in the time T, the following formula (12) is established from the aforementioned formulas (8) and (9):

$$M(glc)(T) = P(glc) \times \int IG(t) \qquad (12)$$

From this relational expression, it is understood that the total quantity M(glc) of the extracted glucose is obtained by multiplying the integrated value of the glucose concentration IG(t) in the tissue fluid at the time t across the time T by the glucose permeability P(glc). The integral of IG(t) can be expressed as an AUC of IG(t) from the formula (10), and hence the following formula (13) is established:

$$M(glc)(T) = P(glc) \times AUC(IG(t)) \qquad (13)$$

From the formula (11), the AUC(IG(t)) can be expressed with the constant number a and the AUC(BG(t)), and hence the following formula (14) is established from the formulas (13) and (11):

$$M(glc) = (P(glc)/a) \times AUC(BG(T)) \qquad (14)$$

In other words, it is understood that the AUC(BG(T)) can be obtained from the total quantity M(glc)(T) of glucose accumulated in the extraction medium within the extraction time T, the permeability of glucose in the extraction time T with respect to the skin (glucose permeability P(glc)) and the constant number a by the aforementioned formula (14). The glucose concentration BG in the blood and the glucose concentration IG in the tissue fluid are substantially equal to each other, and hence in the aforementioned embodiments, all calculations are performed as α=1.

[Advantage of Blood Glucose AUC Measurement Method According to Present Embodiment over Conventional Method]

Figure 23:
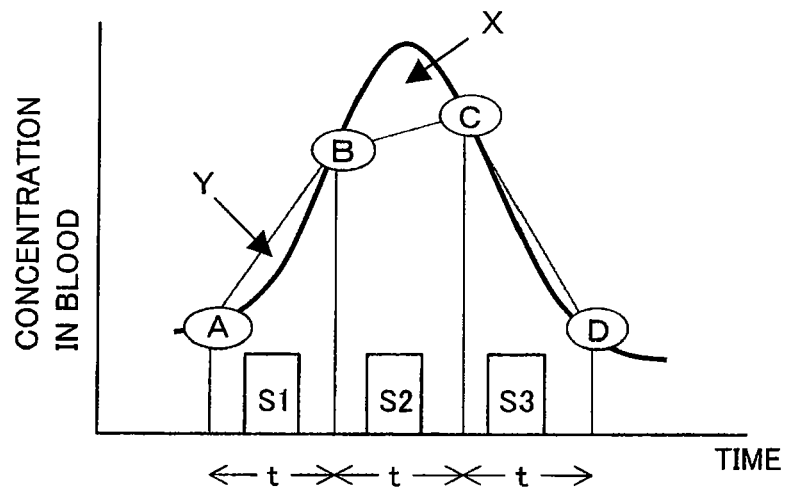
FIG. 23 is a schematic view for illustrating the measurement principle of the blood glucose AUC measurement method by blood drawing.

Next, advantages of a blood glucose AUC measurement method of the present invention over a conventional blood glucose AUC measurement method by blood drawing are described with reference to FIGS. 22 and 23. In FIG. 23, the axis of ordinates shows the glucose concentration in the blood while the axis of abscissas shows time, and a curvilinear graph shows temporal changes of the glucose concentration in the blood. In a case of measuring a blood glucose AUC by blood drawing, glucose concentrations in the blood at a plurality of points are measured by blood drawing. FIG. 23 shows examples where glucose concentrations in the blood A, B, C and D have been obtained as a result of blood drawing every time interval t. The blood glucose AUC by blood drawing is not obtained by integrating the glucose concentrations in the blood across the measurement time but is obtained as an approximate value by summing up areas S1, S2 and S3 of trapezoids surrounded by the respective glucose concentrations in the blood of A to D and the time t. In an example shown in FIG. 23, a blood drawing blood glucose AUC is expressed as the following formula (15):

$$\text{blood drawing blood glucose } AUC = \{(A+B) \times t/2\} + \{(B+C) \times t/2\} + \{(C+D) \times t/2\} \qquad (15)$$

Thus, in a case of measuring the blood glucose AUC by blood drawing, changes of the glucose concentration in the blood are regarded as gradual and rectilinear changes to calculate the blood glucose AUC.

However, an actual glucose concentration in the blood changes contiguously and curvilinearly, as shown in FIGS. 22 and 23. Thus, in a case of regarding the changes of the glucose concentration in the blood as rectilinear changes to measure the blood glucose AUC as in AUC measurement by blood drawing, a portion not reflected in the measurement result, indicated by arrow X or an excess portion indicated by arrow Y in FIG. 23, for example, is generated, and an actual blood glucose AUC and a numerical value of a blood glucose AUC by the conventional method based on the formula (15) differ from each other.

On this point, in the blood glucose AUC measurement method according to each of the first and second embodiments, the tissue fluid is continuously extracted from the start to the end of measurement and the glucose contained in the extracted tissue fluid is accumulated, and hence the glucose quantity reflecting continuous and curvilinear changes of the glucose concentration in the blood is accumulated. Therefore, in the blood glucose AUC measurement method according to each of the first and second embodiments of the present invention, the blood glucose AUC accurately reflecting changes of the glucose concentration in the blood closer to actual changes of the glucose concentration in the blood can be obtained as compared with in the blood glucose AUC measurement method by blood drawing.

[Advantage of Blood Glucose AUC Measurement Method According to Present Embodiment]

According to the first or fifth embodiment, as hereinabove described, the fine pores 601 are formed on the skin 600 to enhance the extraction of the tissue fluid, whereby the tissue fluid can be easily extracted through the site of the skin 600, where the fine pores 601 are formed. Since the tissue fluid containing glucose is extracted from the skin of the subject for as long as 180 minutes and the glucose in the extracted tissue fluid is accumulated, the quantity of glucose correlating with a total quantity of glucose in the circulating blood circulating in the organism within the prescribed period can be accumulated in single measurement. Therefore, it is possible to measure a value (predicted blood glucose AUC) reflecting the total quantity of the glucose circulating in the organism within an extraction time by acquiring a value relating to the quantity of the glucose accumulated by enhancing the extraction of the tissue fluid and extracting the tissue fluid for 180 minutes. It is possible to grasp how long a high concentration state of the measurement target component continues in the organism based on this predicted blood glucose AUC.

While the time for extracting the tissue fluid is set at 180 minutes in the first or fifth embodiment, the present invention is not restricted to this, but the time for extracting the tissue fluid can be arbitrarily set at a range of not less than 60 minutes. It is useful for grasping clinical conditions to measure an area under the blood glucose curve for 60 minutes after sugar load and grasp a high blood glucose state, because it is possible to know an insulin secretion response rate to the sugar load of the subject or the like. A blood glucose level 60 minutes after the sugar load is used as an index for knowing glucose tolerance of the subject. Further, it is possible to grasp blood glucose variable conditions in longer term by setting the extraction time at 120 minutes or more as compared with a case of setting the extraction time at not less than 60 minutes to less than 120 minutes, and it is possible to grasp the blood glucose variable conditions in further longer term by setting the extraction time at 180 minutes or more as compared with a case of setting the extraction time at not less than 60 minutes to less than 180 minutes.

Further, according to the first or fifth embodiment, as hereinabove described, the predicted blood glucose AUC corresponding to the blood drawing blood glucose AUC is obtained, whereby it is possible to obtain a value corresponding to the blood drawing blood glucose AUC without conducting blood drawing, and hence it is possible to grasp clinical conditions of the diabetic subject while reducing a burden on the subject.

According to the first or fifth embodiment, as hereinabove described, the predicted blood glucose AUC is obtained based on the quantity of glucose in the extracted tissue fluid and the amount of an electrolyte in the extracted tissue fluid, whereby it is possible to obtain the predicted blood glucose AUC having high correlativity with the blood drawing blood glucose AUC even when opening of the fine pores varies.

According to the first or fifth embodiment, as hereinabove described, it is possible for the subject to know the end of extraction by a notice of the timer portion 8 by informing the end of extraction by the timer portion 8, and hence it is possible to control a difference between the extraction time and the scheduled time.

According to each of the third and fourth embodiments, as hereinabove described, the gel 801 contains a hypertonic aqueous solution having a higher osmotic pressure than pure water. The tissue fluid is enhanced to move to the gel 801 by osmotic pressure, and hence the tissue fluid can be further enhanced to move to the gel 801 as compared with a case of using the gel 301 containing pure water. Thus, the amount of a measurement target component (glucose) extracted per unit time can be increased.

According to each of the third and fourth embodiments, as hereinabove described, the hypertonic aqueous solution contained in the gel 801 contains the auxiliary component (at least one selected from a group consisting of kalium chloride, glycine and urea) contained with the measurement target component such as glucose in the tissue fluid and different from the measurement target component (glucose), whereby movement of the tissue fluid to the extraction medium can be enhanced without changing the measurement results of the measurement target component.

According to each of the third and fourth embodiments, as hereinabove described, at least one is selected from a group consisting of kalium chloride, glycine and urea as the auxiliary component, whereby the hypertonic aqueous solution having a higher osmotic pressure than pure water can be obtained using at least one of kalium chloride, glycine and urea contained in the tissue fluid in a slight amount. Thus, the hypertonic aqueous solution having a higher concentration (osmotic pressure) than the concentration of the auxiliary component in the tissue fluid can be easily obtained.

According to each of the third and fourth embodiments, as hereinabove described, the concentration of the auxiliary component is set at 0.2 mM (mmol/L) or more, whereby the concentration (osmotic pressure) of the hypertonic aqueous solution containing at least one of kalium chloride, glycine and urea can be rendered higher than the concentrations of kalium chloride, glycine and urea each contained in the tissue fluid in a slight amount and each having few differences in the content thereof in the tissue fluid among individuals.

The remaining effects of the third embodiment are similar to those of the aforementioned first embodiment.

EXAMPLE

Example 1

Example of Blood Glucose AUC Measurement of Plurality of Specimens Using Pure Water A predicted blood glucose AUC was measured according to the second embodiment of the present invention.

1. Pretreatment to Extraction of Tissue Fluid

First, a plurality of specimens (subjects) were pretreated by the method as described in the explanation of the second embodiment (pretreatment step). More specifically, the fine pores 601 (see FIG. 9) were formed on a total of 51 sites of seven specimens by the puncture device 400 (see FIG. 7).

Next, the tissue fluid was extracted through the skin where the fine pores are formed by the method as described in the explanation of the second embodiment (extraction-accumulation step). 100 µL of pure water is used for extraction of the tissue fluid, and the extraction of the tissue fluid was performed by setting the extraction time at 60 minutes, 120 minutes, 180 minutes and 300 minutes.

2. Measurement of Blood Drawing Blood Glucose AUC

Blood drawing was performed every 15 minutes in parallel with the extraction of the tissue fluid, and a blood glucose AUC by blood drawing was measured.

3. Calculation of Extraction Glucose Quantity

A fluid to which the tissue fluid is extracted was collected, and a glucose concentration C(glc) was measured from the collected fluid using a glucose oxidase measurement method. The extraction glucose quantity M(glc) was calculated from the glucose concentration C(glc) obtained here and the volume (100 μL) of pure water based on the aforementioned formula (2).

4. Measurement of Sodium Ion Concentration

Figure 24:
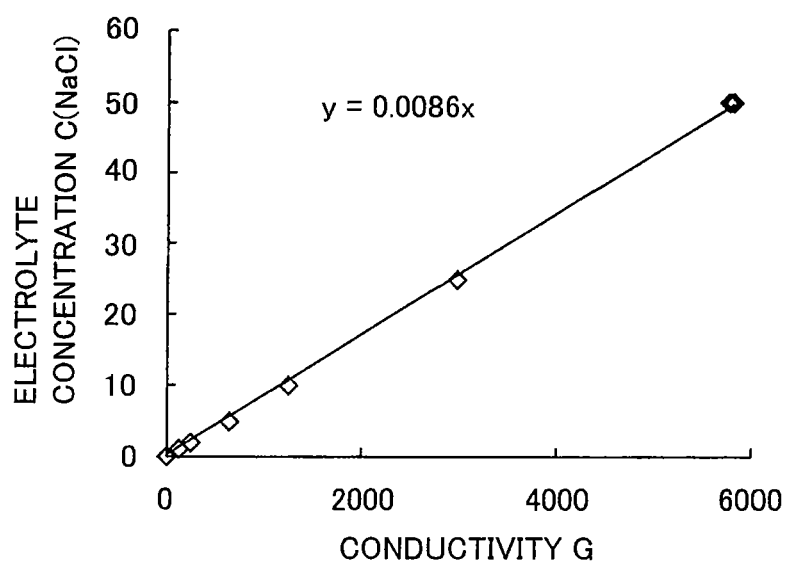
FIG. 24 is a graph showing a correlation between an electrolyte concentration and a conductivity in a case where tissue fluid is extracted in pure water.

Next, a conductivity G of the collected fluid was measured. A conductivity meter (DS-51: manufactured by HORIBA, Ltd.) was used in the measurement of the conductivity G. FIG. 24 is a graph showing a correlation between the conductivity G and an electrolyte concentration C(NaCl). It is clear from the graph of FIG. 24 that the electrolyte concentration C(NaCl) can be calculated using the conductivity G. The following formula (16) was obtained as an approximation formula from a relation between the conductivity G and the electrolyte concentration C(NaCl) shown in FIG. 24, and the electrolyte concentration C(NaCl) was calculated from the conductivity G using this formula:

$$C(NaCl) = 0.0086 \times G \tag{16}$$

5. Calculation of Glucose Permeability

5-1. Calculation of True Glucose Permeability P'(glc)

A true glucose permeability P'(glc) was obtained from the blood drawing blood glucose AUC measured in 2. and the extraction glucose quantity M(glc) calculated in 3. based on the following formula:

$$P'(glc) = M(glc)/AUC(BG)$$

5-2. Calculation of Electrolyte Extraction Rate J

Next, an electrolyte extraction rate J was calculated using the electrolyte concentration C(NaCl) obtained in 4. based on the formula (4).

5-3. Determination of Constant Numbers E and F

When calculating a predicted glucose permeability P(glc) based on the electrolyte extraction rate J obtained in 5-2. and the formula (5), constant numbers E and F were determined as described below.

Figure 25:
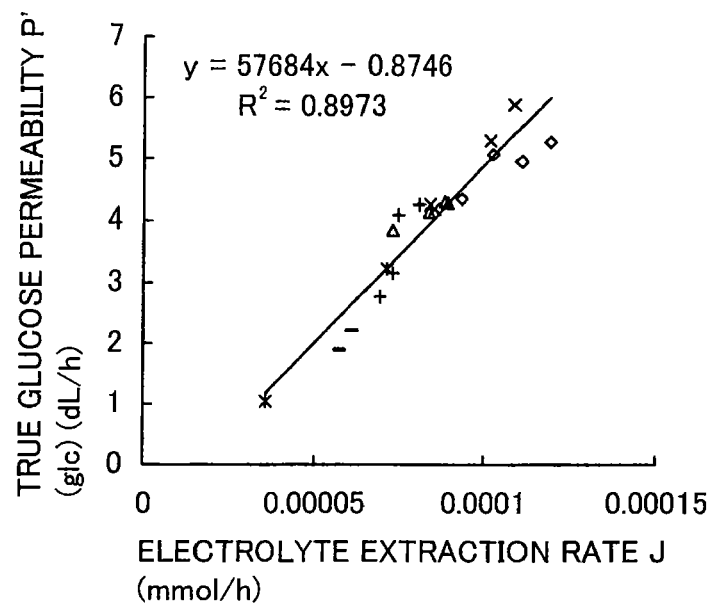
FIG. 25 is a graph showing a correlation between an electrolyte extraction rate and a glucose permeability in a case where the measurement time is 60 minutes.
Figure 26:
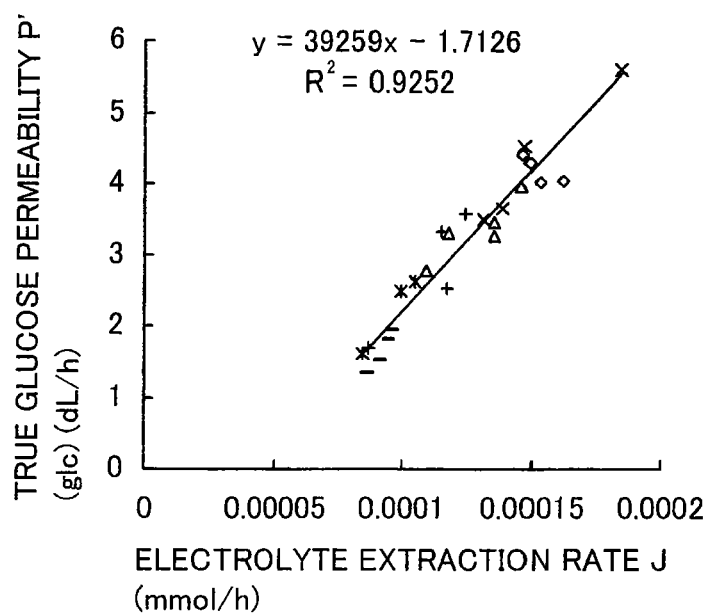
FIG. 26 is a graph showing a correlation between an electrolyte extraction rate and a glucose permeability in a case where the measurement time is 120 minutes.
Figure 27:
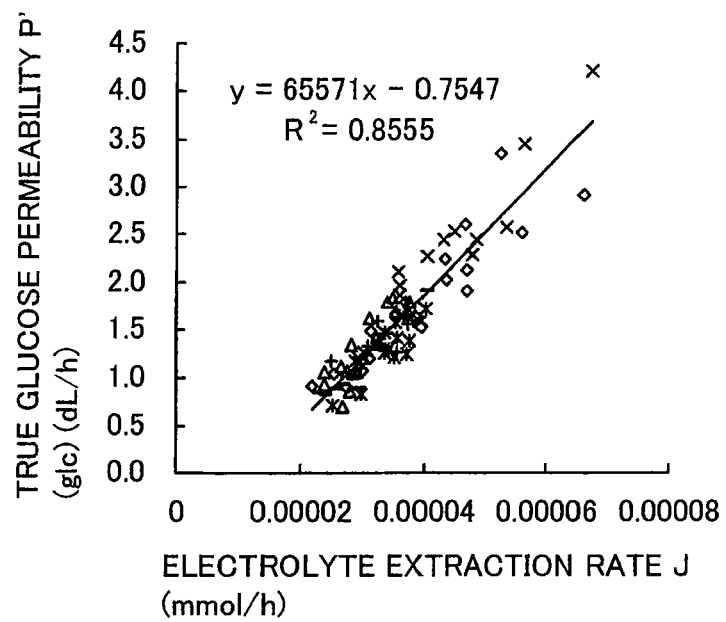
FIG. 27 is a graph showing a correlation between an electrolyte extraction rate and a glucose permeability in a case where the measurement time is 180 minutes.

FIGS. 25 to 27 are graphs showing a correlation between an electrolyte extraction rate J and a true glucose permeability P'(glc) in each of cases where the measurement times are 60 minutes, 120 minutes and 180 minutes. In the graphs of FIGS. 25 to 27, the axis of ordinates and the axis of abscissas show the true glucose permeability P'(glc) and the electrolyte extraction rates J, respectively. In the graphs of FIGS. 25 to 27, correlation coefficients between the true glucose permeability P'(glc) and the electrolyte extraction rate J are 0.8973, 0.9252 and 0.8555 and show a high correlation. This is conceivably for the following reason. In other words, the electrolyte stably exists in the body and exists also in the tissue fluid at a substantially constant concentration. Therefore, the electrolyte extraction rate is large in a case where the fine pores 601 are large, and the electrolyte extraction rate is small in a case where the fine pores 601 are small, and hence an electrolyte extraction rate J(ion) conceivably reflects the state of the fine pores 601. On the other hand, the state of the fine pores 601 is conceivably reflected also in the ease of extracting glucose, that is a glucose permeability P'(glc). Thus, a high correlation has been conceivably shown between the electrolyte extraction rate J(ion) and the glucose permeability P'(glc).

It is clear from this result that a value capable of substituting for the true glucose permeability P'(glc) can be obtained if the electrolyte extraction rate J is approximated to calculate the predicted glucose permeability P(glc).

In this example, the constant numbers E and F for approximating the electrolyte extraction rate J were calculated and the following values were obtained in each of cases where the measurement times are 60 minutes, 120 minutes and 180 minutes.

| Extraction Time (Minute) | Constant Number E | Constant Number F |
|---|---|---|
| 60 | 57684 | −0.8746 |
| 120 | 39259 | −1.7126 |
| 180 | 65571 | −0.7547 |

5-4. Calculation of Predicted Glucose Permeability P(glc)

A predicted glucose permeability P(glc) was calculated using the obtained constant numbers E and F and the extraction rate J obtained in 5-2. based on the formula (5).

5-5. Verification of Accuracy of Predicted Glucose Permeability

The predicted glucose permeability P(glc) obtained in 5-4. and the true glucose permeability P'(glc) obtained in 5-1. were compared with each other in order to verify the accuracy of the predicted glucose permeability P(glc) calculated according to this example. The comparison results have been shown in FIG. 28.

Figure 28:
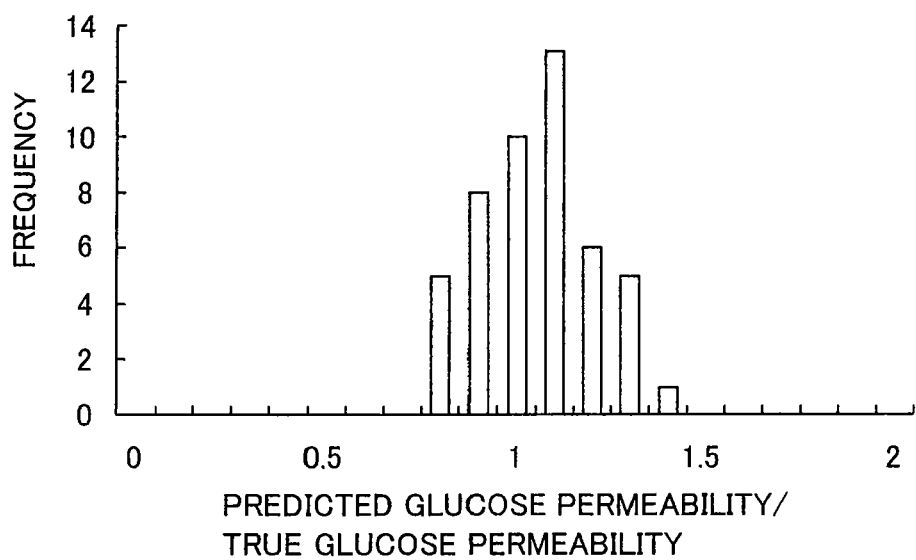
FIG. 28 is a histogram showing the frequencies of ratios of a predicted glucose permeability to a true glucose permeability.

FIG. 28 is a histogram in which the axis of abscissas shows ratios of a glucose permeability calculated using the aforementioned formula (5) to a true glucose permeability P'(glc) and the axis of ordinates shows the frequencies of the ratios. As shown in FIG. 28, a frequency is high when values of ratios of a predicted glucose permeability to a true glucose permeability are close to 1, and it is understood that the true glucose permeability and the predicted glucose permeability are approximate to each other.

6. Calculation of Predicted Blood Glucose AUC

Next, a predicted blood glucose AUC (predicted AUC) was calculated using the glucose quantity M(glc) obtained in 3. and the predicted glucose permeability P(glc) obtained in 5. based on the aforementioned formula (6).

7. Verification of Correlativity Between Predicted Blood Glucose AUC and Blood Drawing Blood Glucose AUC Next, a correlation between a predicted blood glucose AUC actually measured using the measurement method according to the aforementioned second embodiment and a blood drawing blood glucose AUC by blood drawing is described with reference to FIGS. 7, 9 and 24 to 28. A correlation coefficient R is a value from −1 to 1 for expressing correlative strength between a vertical axis parameter and a horizontal axis parameter in the following explanation, and the absolute value closer to 1 expresses the higher correlation. In a case where respective plots all lie on the same straight line, the correlation coefficient is 1 or −1.

Figure 29:
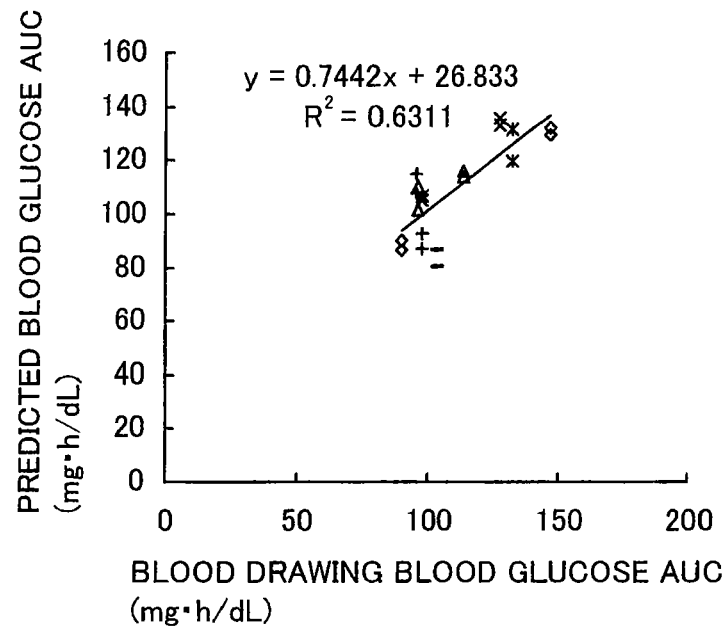
FIG. 29 is a graph showing a correlation between a blood drawing blood glucose AUC and a predicted blood glucose AUC in a case where the measurement time is 60 minutes.
Figure 30:
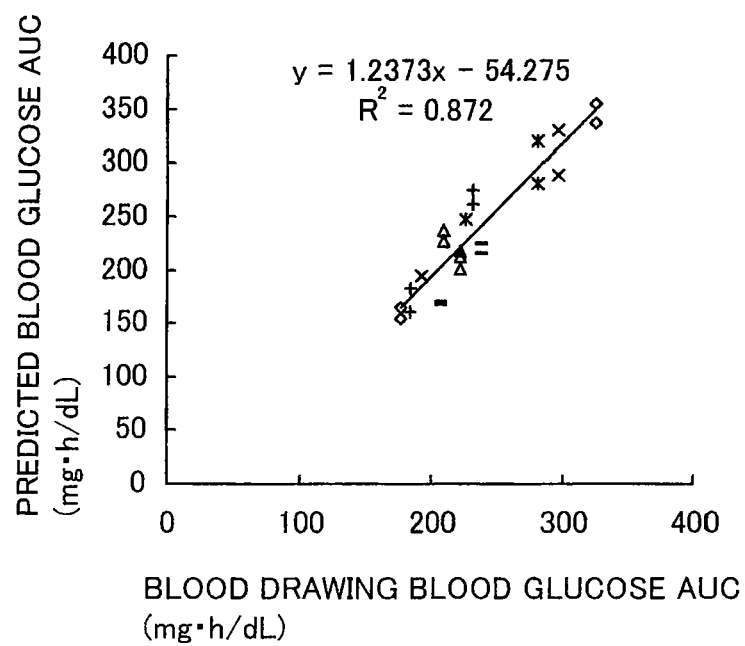
FIG. 30 is a graph showing a correlation between a blood drawing blood glucose AUC and a predicted blood glucose AUC in a case where the measurement time is 120 minutes.
Figure 31:
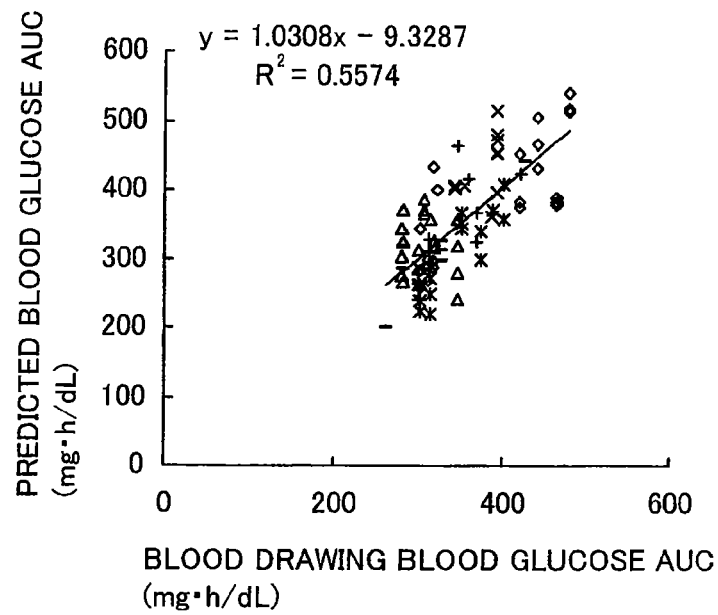
FIG. 31 is a graph showing a correlation between a blood drawing blood glucose AUC and a predicted blood glucose AUC in a case where the measurement time is 180 minutes.

Relations between the predicted blood glucose AUC and the blood drawing blood glucose AUC obtained according to Example 1 in respective cases where the extraction times are 60 minutes, 120 minutes and 180 minutes were plotted on graphs, and the correlativity was considered. The graphs are shown in FIGS. 29 to 31. In the graphs of FIGS. 29 to 31, the axis of abscissas and the axis of ordinates show blood drawing blood glucose AUCs and predicted blood glucose AUCs, respectively.

As shown in FIGS. 29 to 31, in each of cases where the extraction times are 60 minutes, 120 minutes and 180 minutes, the correlation between the predicted blood glucose AUC and the blood drawing blood glucose AUC was as follows:

| Extraction Time (Minute) | Correlation Coefficient |
|---|---|
| 60 | 0.6311 |
| 120 | 0.872 |
| 180 | 0.5574 |

It is clear from these results that the predicted blood glucose AUC and the blood drawing blood glucose AUC have a high correlation with each other in a case where the extraction time is at least 60 minutes. These results suggested that a value of the predicted blood glucose AUC obtained without blood drawing according to the first and second embodiments can be used instead of the blood drawing blood glucose AUC calculated through blood drawing.

It has been verified by the aforementioned experiment that a blood glucose AUC having accuracy, capable of substituting for the blood glucose AUC obtained by blood drawing can be measured by the measurement method according to each of the first and second embodiments.

8. Verification of Change of Measurement Value Based on Extraction Time, of Predicted Blood Glucose AUC Next, consideration results of changes of measurement values based on extraction times, of the blood glucose AUC measured according to each of the first and second embodiments are described with reference to FIG. 32. In the following explanation, a blood drawing blood glucose AUC based on measurement for X minutes and a predicted blood glucose AUC based on extraction for X minutes are referred to as a blood drawing blood glucose AUC (X) and a predicted blood glucose AUC (X), respectively.

Figure 32:
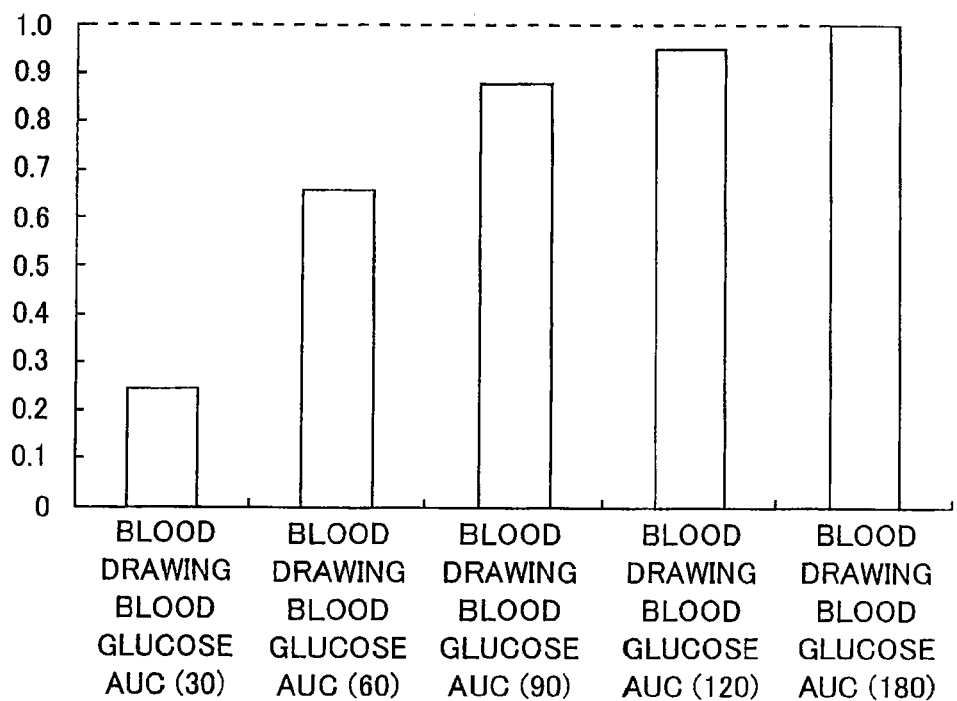
FIG. 32 is a graph showing a correlation between a blood drawing blood glucose AUC (180), a blood drawing blood glucose AUC (30), a blood drawing blood glucose AUC (60), a blood drawing blood glucose AUC (90) and a blood drawing blood glucose AUC (120).

A blood drawing blood glucose AUC (180) is the most commonly used as an index for grasping the clinical conditions of the diabetic subject or predicting the amount of drug taken into the body. Under the premise that the blood drawing blood glucose AUC (180) is the most ideal value, a correlation between the blood drawing blood glucose AUC (180) and a blood drawing blood glucose AUC (X (X=30, 60, 90, 120)) was considered. As shown in FIG. 32, it is clear that a blood drawing blood glucose AUC of 60 minutes or more has a high correlation with the blood drawing blood glucose AUC (180). On the other hand, it is clear that a blood drawing blood glucose AUC of less than 60 minutes has a low correlation with the blood drawing blood glucose AUC (180).

Thus, it was suggested that a value showing a high correlation with a blood glucose AUC (180), which is an ideal value, can be measured by measuring a blood glucose AUC of 60 minutes or more. Based on these findings, a predicted blood glucose AUC reflecting the blood glucose AUC (180), which is an ideal value, can be conceivably obtained by going through an extraction step for 60 minutes or more also in the measurement method according to each of the first and second embodiments.

Thus, it has been verified that a predicted blood glucose AUC having a high correlation with the blood drawing blood glucose AUC (180), which is an ideal value, can be acquired by setting the extraction time at 60 minutes or more in the measurement method according to each of the first and second embodiments and each of a predicted blood glucose AUC (60) to a predicted blood glucose AUC (180) can be used as an index for grasping the clinical conditions of the diabetic subject instead of the blood drawing blood glucose AUC (180).

As shown in FIGS. 29 to 31, a correlation between a predicted blood glucose AUC and a blood drawing blood glucose AUC is high regardless of an extraction time (60 minutes, 120 minutes and 180 minutes), and hence any of the predicted blood glucose AUC (60), the predicted blood glucose AUC (120) and the predicted blood glucose AUC (180) can be conceivably used as a highly-reliable index in grasping the clinical conditions of the diabetic subject. A correlation with the blood drawing blood glucose AUC (180), which is an ideal value, is increased in order of the blood drawing blood glucose AUC (60) and the blood drawing blood glucose AUC (120), and hence it is conceivably more preferable to use a value of the predicted blood glucose AUC (120) than a value of the predicted blood glucose AUC (60) as an index actually used and it is conceivably more preferable to use a value of the predicted blood glucose AUC (180) than a value of the predicted blood glucose AUC (120) as an index actually used.

Example 2

Example of Blood Glucose AUC Measurement of Single Specimen Using Pure Water

Example 1 suggested that the predicted blood glucose AUC (180) having a high correlation with the blood drawing blood glucose AUC (180) can be acquired by setting the extraction time at 180 minutes or more in the measurement method according to the second embodiment. Example 2 where a predicted blood glucose AUC is measured by setting the extraction time at 180 minutes under the same measurement conditions as those shown in Example 1 is now described.

Similarly to Example 1, tissue fluid was extracted from a specimen for 180 minutes or more using 100 μL of pure water. Blood drawing was performed every 15 minutes in parallel with the extraction of the tissue fluid.

A glucose concentration C(glc) and an electrolyte concentration C(NaCl) were measured from the extracted tissue fluid in the same manner as Example 1. The measurement result is as follows:

Glucose Concentration C(glc) 5686 ng/mL
Electrolyte Concentration C(NaCl) 3.6 mM (mmol/L)

When a blood drawing blood glucose AUC (180) was measured with blood obtained by collection from this specimen, the blood drawing blood glucose AUC (180) was 358 mg·h/dL.

An extraction glucose quantity M(glc) was calculated from the glucose concentration C(glc) obtained by measuring the extracted tissue fluid based on the formula (2). In other words, the extraction glucose quantity M(glc) was calculated with the following formula (17):

$$M(glc)=5686(ng)\times 100/1000(mL) \qquad (17)$$

Thus, a result of M(glc)=568.6 ng was obtained.

Next, an electrolyte extraction rate J was calculated from the obtained electrolyte concentration C(NaCl) based on the formula (4). In other words, the electrolyte extraction rate J was calculated with the following formula (18):

$$J=3.6(mM)\times 100\times 10^{-6}(L)\times \frac{1}{3}(time:h) \qquad (18)$$

Thus, a result of J=1.2×10⁴ (mmol/h) was obtained.

Next, a glucose permeability P(glc) was calculated from the obtained electrolyte extraction rate J based on the formula (5). In this example, values of 13474 and −0.0327 were used as the constant numbers E and F, respectively, used in the formula (5). In other words, the glucose permeability P(glc) was calculated with the following formula (19):

$$P(glc)=13474\times 1.2\times 10^4 (mmol/h)-0.327 \qquad (19)$$

Thus, a result of P(glc)=1.58(10⁻⁶ dL/h) was obtained.

Next, a predicted blood glucose AUC (predicted AUC) was calculated from the aforementioned obtained extraction glucose quantity M(glc) and glucose permeability P(glc) based on the formula (6). In other words, the predicted blood glucose AUC was calculated with the following formula (20):

$$\text{predicted } AUC = 568.6(\text{ng})/1.58 \times 10^{-6}(\text{dL/h}) \quad (20)$$

Thus, a result of predicted AUC=360 mg·h/dL was obtained. It is understood that this value is a value very approximate to the measurement value (358 mg·h/dL) of the aforementioned blood drawing blood glucose AUC. Thus, it has been verified that an accurate blood glucose AUC capable of substituting for the blood drawing blood glucose AUC (180), which is an ideal value, can be measured according to Example 2.

Example 3

Example of Blood Glucose AUC Measurement of Single Specimen Using Hypertonic Aqueous Solution An example where a blood glucose level is calculated by the measurement method according to the fourth embodiment is described. The extraction time is set at 3 hours (180 minutes), and an alarm timer was used as time informing means. Actual measurement values of an specimen A used in an experiment were as follows:

| Actual Measurement Value of Specimen A | |
|---|---|
| Extraction Glucose Concentration: | 4615 ng/ml |
| KCl Aqueous Solution: | 100 μl |
| Extraction Electrolyte Concentration: | 2.415 mM |
| Area under Curved (Blood Drawing Measurement Method): | 358 mg · h/dl |

An extraction glucose quantity M(glc) was obtained from the aforementioned formula (2) as:

$$M(glc) = (\text{extraction glucose concentration}) \times$$
$$(\text{KCl aqueous solution})$$
$$= 4615 \times 100/1000$$
$$= 461.5 \text{ ng}$$

An electrolyte (sodium ion) extraction rate J was obtained from the aforementioned formula (4) as:

$$J = (\text{electrolyte concentration}) \times$$
$$(\text{KCl aqueous solution})/(\text{extraction time})$$
$$= 2.415 \times 10^3 \times 100 \times 10^{-6}/3$$
$$= 8.05 \times 10^{-2} (\mu\text{mol/h})$$

Then, a glucose permeability P(glc) was obtained from the aforementioned formula (5) as:

$$P(glc) = \alpha \times (\text{electrolyte extraction rate}) + \beta$$
$$= 16.987 \times 8.05 \times 10^{-2} - 0.0948$$
$$= 1.27 (10^{-6} \cdot \text{dl/h})$$

Figure 33:
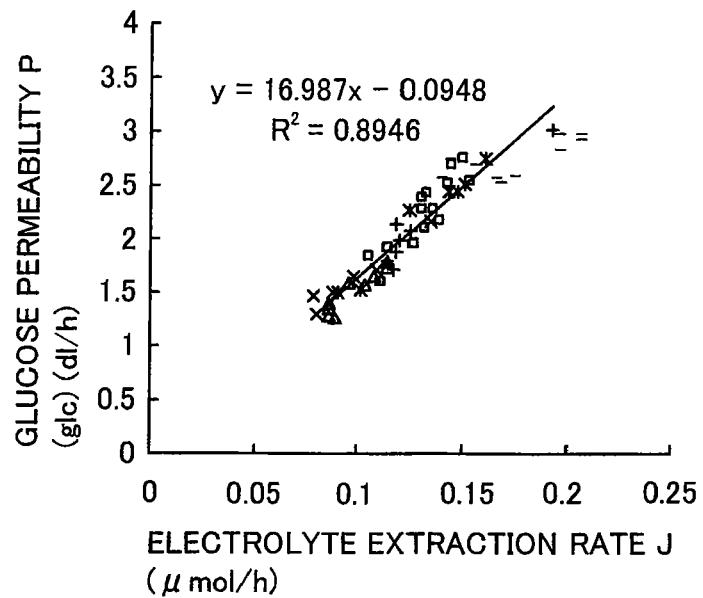
FIG. 33 is a diagram showing a relation between a glucose permeability and an electrolyte extraction rate.

As shown in FIG. 33, values of α=16.987 and β=−0.0948 are values obtained by an experiment similarly to the aforementioned Example 2 (see FIGS. 25 to 27). A correlation coefficient R between the glucose permeability P(glc) and the electrolyte extraction rate J is 0.8946 in Example 3, which has showed a high correlation similarly to the aforementioned Example 2.

Next, a predicted blood glucose AUC (predicted AUC) was calculated with the aforementioned formula (6):

$$\text{predicted } AUC = M(glc)/P(glc)$$
$$= 461.5/(1.27 \times 10^{-6})$$
$$= 363.4 (\text{mg·h/dl})$$

The predicted blood glucose AUC (predicted AUC) calculated in this way is a value approximate to 358 mg·h/dl of a laboratory value obtained from an area under the curve by separate blood drawing (measurement method by blood drawing).

Example 4

Example of Blood Glucose AUC Measurement of Plurality of Specimens Using Hypertonic Aqueous Solution 1. Measurement of Blood Glucose AUC In Example 4, it is described by the following experiment that an area under the blood glucose time curve (blood glucose AUC (60)) for 60 minutes after sugar load in a case where the extraction time is 60 minutes and an area under the blood glucose time curve (blood glucose AUC (120)) for 120 minutes after sugar load in a case where the extraction time is 120 minutes are predictable in an example where a hypertonic aqueous solution (KCl aqueous solution) is used as an extraction solvent. In FIGS. 34 to 39, difference of plot symbols shows difference of specimens.

Figure 34:
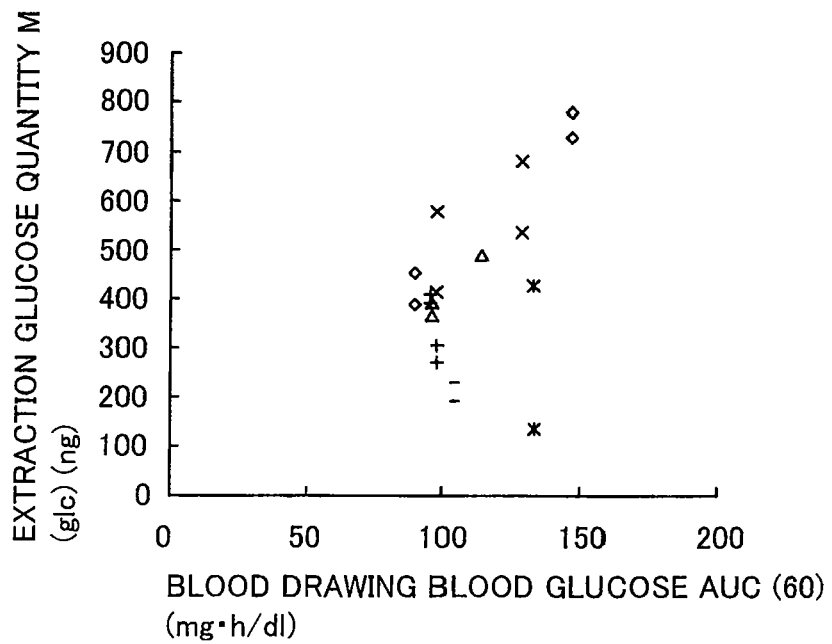
FIG. 34 is a graph showing a correlation between the blood drawing blood glucose AUC (60) and the extraction glucose quantity.
Figure 35:
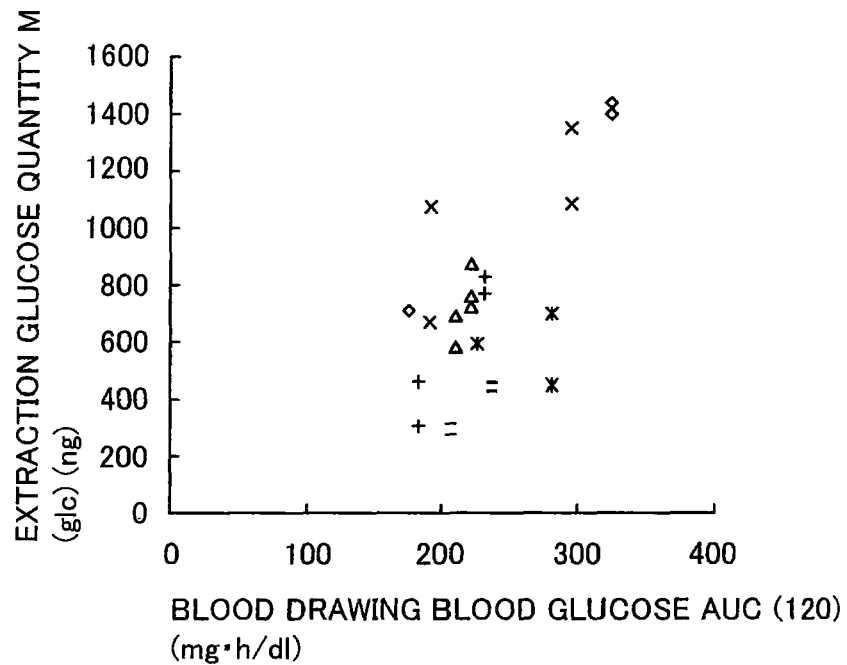
FIG. 35 is a graph showing a correlation between the blood drawing blood glucose AUC (120) and the extraction glucose quantity.

An experiment method is as follows:
[Experiment Condition]
Extraction Solvent: KCl aqueous solution 70 mM, 90 μL
Extraction Form: liquid chamber (collection member)
Extraction Area: 5 mm×10 mm
Extraction Time: 60 minutes and 120 minutes
Number of Specimens: 6
Number of Sites: 22
Glucose Measurement Method: GOD fluorescence absorbance method
Sodium Ion Measurement Method: HPLC measurement
Fine Needle Array Shape: length of fine needle=300 μm, number of fine needles=305 pieces
Puncturing Rate: 6 m/s
Blood Glucose Measurement Method: measurement of forearm SMBG value at 15-minute intervals
Blood Glucose AUC Measurement Method: calculation based on forearm SMBG value by trapezoidal approximation method First, calculation methods of a blood glucose AUC (60) and a blood glucose AUC (120) are shown. A relation between each of a blood drawing blood glucose AUC (60) and a blood drawing blood glucose AUC (120), and the extraction glucose quantity M(glc) is shown in FIGS. 34 and 35.

The following relational formula is established between the extraction glucose M(glc) and a blood glucose AUC (X)

(area under the blood glucose time curve for X minutes after sugar load), as expressed in the aforementioned formula (14):

$$M(glc)=P(glc) \times \text{blood glucose } AUC(X) \quad (21)$$

Figure 36:
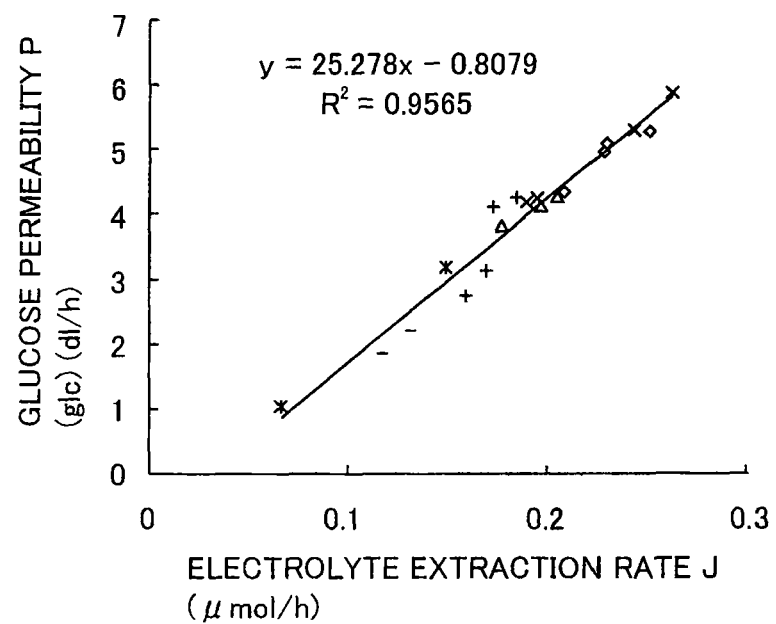
FIG. 36 is a graph showing a correlation (for 60 minutes) between a glucose permeability and a sodium ion extraction rate.
Figure 37:
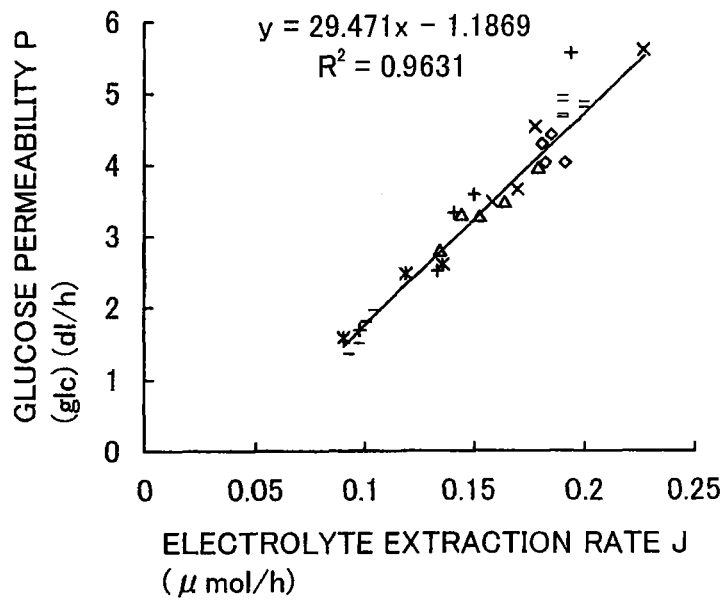
FIG. 37 is a graph showing a correlation (for 120 minutes) between a glucose permeability and a sodium ion extraction rate.

Correlativity shown in FIGS. 36 and 37 was found between this glucose permeability P(glc) and an electrolyte extraction rate J calculated from an electrolyte (sodium ion) concentration of the extraction solvent.

Glucose permeability P(glc)s in extraction for 60 minutes and 120 minutes are calculated from the following formulas (22) and (23) based on the aforementioned formula (5) using this correlativity:

In Extraction for 60 Minutes:

$$P(glc)=\alpha \times J+\beta (\alpha=25.278, \beta=0.8079) \quad (22)$$

In Extraction for 120 Minutes:

$$P(glc)=\alpha \times J+\beta (\alpha=29.471, \beta=0.1869) \quad (23)$$

Predicted blood glucose AUCs in extraction for 60 minutes and 120 minutes (a predicted AUC (60) and a predicted AUC (120)) were predicted from the aforementioned formula (6) using the glucose permeability P(glc)s obtained by the aforementioned formulas (22) and (23).

Figure 38:
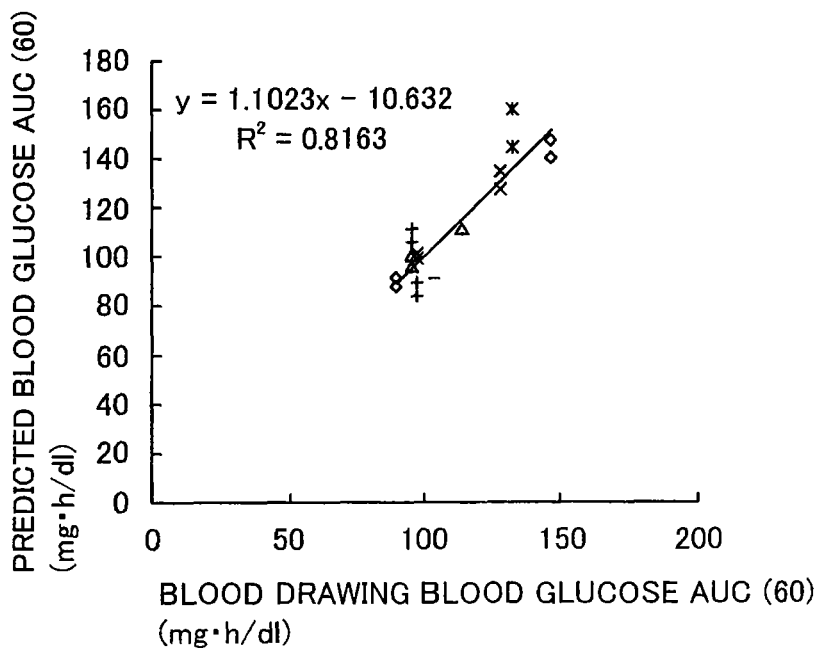
FIG. 38 is a graph showing a correlation between the blood drawing blood glucose AUC (60) and a predicted blood glucose AUC (60).
Figure 39:
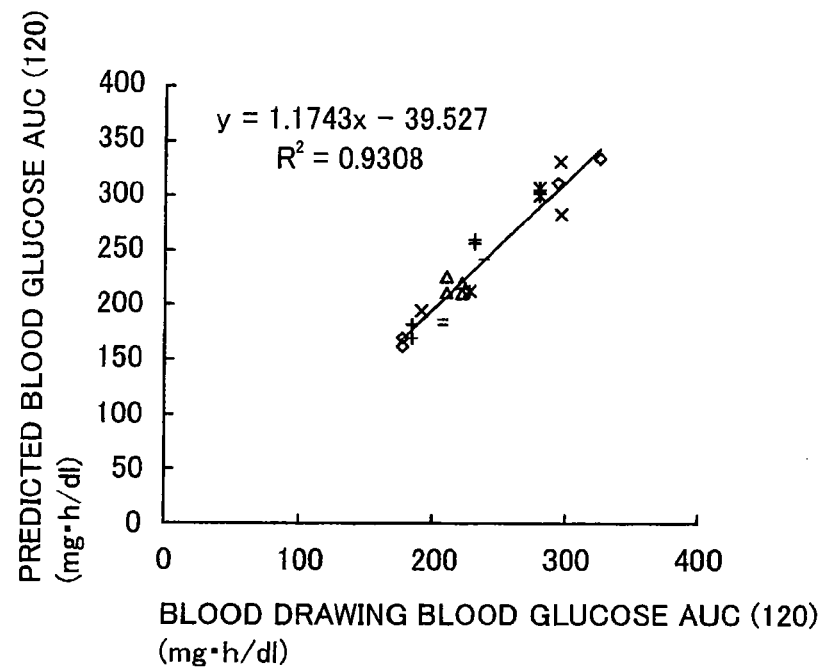
FIG. 39 is a graph showing a correlation between the blood drawing blood glucose AUC (120) and a predicted blood glucose AUC (120).

Correlativity between the obtained predicted AUC (60) and the blood drawing blood glucose AUC (60) obtained from the blood glucose level, and the predicted AUC (120) and the blood drawing blood glucose AUC (120) obtained from the blood glucose level is shown in FIGS. 38 and 39.

These results have shown that a blood glucose AUC (60) and a blood glucose AUC (120) can be measured by this method because high values of correlation coefficient Rs=0.8163 and 0.9308 are obtained.

Figure 40:
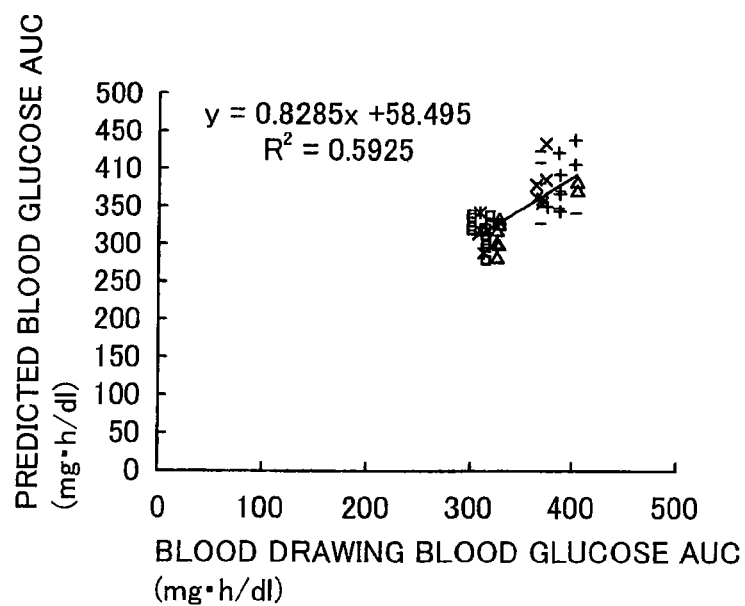
FIG. 40 is a diagram showing a relation between a blood drawing blood glucose AUC and a predicted blood glucose AUC.

For reference, high correlativity existed between measurement results of a blood drawing blood glucose AUC for 180 minutes by blood drawing and a predicted blood glucose AUC for 180 minutes according to the present invention because the correlation coefficient R is 0.5925 in the graph showing a correlation therebetween, as shown in FIG. 40.

2. Verification of Significance in Case of Using KCL Aqueous Solution

Figure 41:
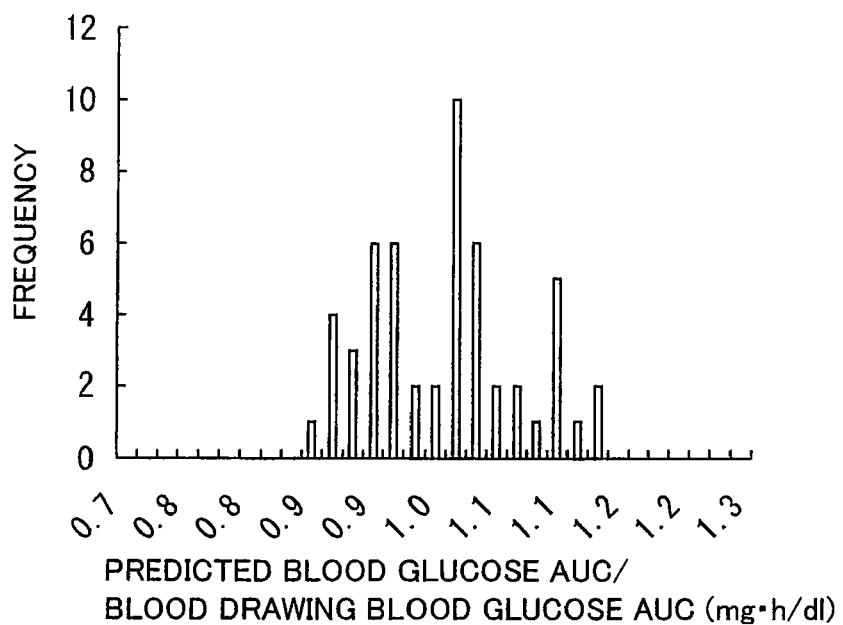
FIG. 41 is a diagram showing a distribution of measurement errors of a blood glucose AUC in a case of using a kalium chloride aqueous solution as an extraction medium.
Figure 42:
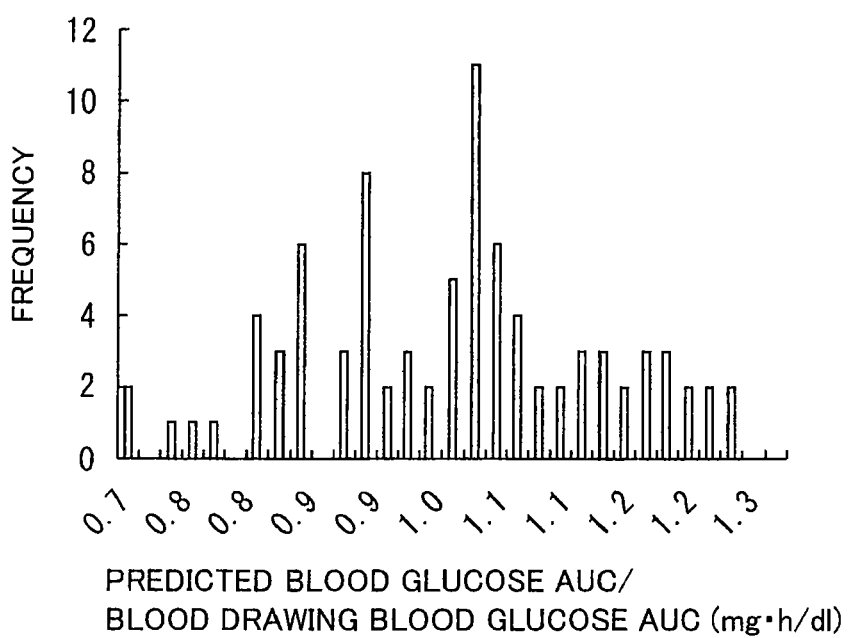
FIG. 42 is a diagram showing a distribution of measurement errors of a blood glucose AUC in a case of using pure water as an extraction medium.

Next, a correlation between the predicted blood glucose AUC (predicted AUC) actually measured by the measurement method according to the fourth embodiment and the blood drawing blood glucose AUC by blood drawing is described using an example. FIGS. 40 to 42 are diagrams for illustrating a correlation between the predicted blood glucose AUC (predicted AUC) in the fourth embodiment of the present invention and the blood drawing blood glucose AUC by blood drawing.

Prediction accuracy of the predicted blood glucose AUC in a case of using a hypertonic aqueous solution (KCl aqueous solution) as an extraction solvent was verified. Experiment conditions are as follows, and in Example 4, a concentration of a KCl solvent was adjusted to 70 mM and an osmotic pressure of the solvent was adjusted to 140 mOsm/L:

[Experiment Condition]
Extraction Solvent: KCl aqueous solution 70 mM, 90 μL,
Extraction Form: liquid chamber (collection member)
Extraction Area: 5 mm×10 mm
Extraction Time: 180 minutes
Number of Specimens (Subjects): 7
Number of Sites: 80
Glucose Concentration Measurement Method: GOD fluorescence absorbance method
Sodium Ion Concentration Measurement Method: ion chromatograph
Fine Needle Array Shape: length of fine needle=300 μm, number of fine needles=305 pieces
Puncturing Rate: 6 m/s
Blood Glucose Measurement Method: measurement of forearm SMBG value at 15-minute intervals
Blood Glucose AUC Measurement Method: calculation based on forearm SMBG value by trapezoidal approximation method A glucose permeability P(glc) was calculated from an electrolyte extraction rate J using the formula (5), similarly to the aforementioned Example 3. A predicted blood glucose AUC (predicted AUC) was calculated from the obtained glucose permeability P(glc) and extraction glucose quantity M(glc) using the aforementioned formula (6).

FIG. 40 shows correlativity between the predicted blood glucose AUC calculated using the aforementioned formula (6) and the blood drawing blood glucose AUC obtained by blood drawing. As shown in FIG. 40, the blood drawing blood glucose AUC and the predicted blood glucose AUC have correlativity of a correlation coefficient R=0.5925 with each other.

In order to evaluate accuracy of the predicted blood glucose AUC, a ratio r of a measurement value to a true value was calculated as follows:

$$r=\text{predicted blood glucose } AUC/\text{blood drawing blood glucose } AUC$$

Accuracy of the aforementioned measurement system was evaluated by evaluating what degree of dispersion this r has around 1 as a center. The distribution of r in FIG. 40 is shown in FIG. 41.

Here, a comparative experiment was performed under the same experiment conditions as described above except for using pure water instead of a hypertonic aqueous solution (KCl aqueous solution). The distribution of blood glucose AUC measurement error corresponding to FIG. 41 was obtained based on results of this comparative experiment. The results are shown in FIG. 42.

When differences in distribution of measurement error in FIGS. 41 (KCl aqueous solution) and 42 (pure water) were evaluated by F test, a significant difference of $P<0.005$ was recognized. In other words, it was found that measurement accuracy of a blood glucose AUC in a case of using the hypertonic aqueous solution (KCl aqueous solution) as an extraction medium is higher than that in a case of using an extraction medium of pure water.

Figure 43:
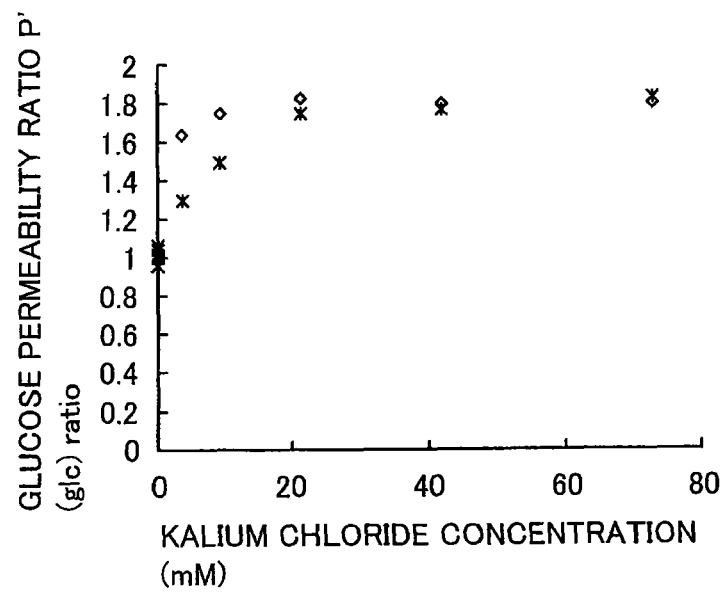
FIG. 43 is a diagram showing dependence of a glucose permeability on a concentration of a kalium chloride aqueous solution.

3. Verification of Change of Glucose Permeability Based on KCL Aqueous Solution Concentration Next, what extent a glucose permeability P(glc) is improved in a case of using the hypertonic aqueous solution (KCl aqueous solution) as an extraction medium has been verified by performing an extraction experiment in which a concentration of the KCl aqueous solution (a concentration of an auxiliary component in the hypertonic aqueous solution) is variously changed. Experiment conditions are as follows:

[Experiment Condition]
Extraction Solvent: KCl aqueous solution (5, 10, 20, 40, 70 mM)
Extraction Solvent Quantity: 90 μL,
Extraction Form: liquid chamber (collection member)
Extraction Area: 5 mm×10 mm
Extraction Time: 15 minutes
Number of Specimens (Subjects): 1
Measurement Site: 3
Glucose Measurement Method: GOD fluorescence absorbance method
Sodium Ion Measurement Method: ion chromatograph Fine Needle Array Shape: length of fine needle=300 μm, number of fine needles=305 pieces Puncturing Rate: 6 m/s Blood Glucose Measurement Method: measurement of forearm SMBG value at 15-minute intervals Blood Glucose AUC Measurement Method: calculation based on forearm SMBG value by trapezoidal approximation method A true glucose permeability P'(glc) was calculated from the extraction glucose quantity M(glc) and the blood drawing blood glucose AUC both obtained by this experiment based on the aforementioned formula (6). Further, a glucose permeability ratio (P'(glc) ratio), which is a value obtained by standardizing a true glucose permeability P'(glc) in using each extraction solvent with a true glucose permeability P'(glc) in extraction using pure water as an extraction medium each extraction solvent, was calculated, and a relation with the concentration of the auxiliary component (kalium chloride) in the hypertonic aqueous solution was evaluated. The results are shown in FIG. 43. In FIG. 43, difference of plot symbols shows difference of sites.

It is clear from FIG. 43 that the osmotic pressure of the medium is increased when the concentration of KCl serving as an auxiliary component is 5 mM or more in the extraction medium, and the glucose permeability is improved as compared with a case of extraction using an extraction medium of pure water. A relation between the concentration of the auxiliary component (kalium chloride) and the osmotic pressure in FIG. 43 is as follows:

| Kalium Chloride Concentration | Osmotic Pressure |
| --- | --- |
| 5 mM | 10 mOsm/l |
| 10 mM | 20 mOsm/l |
| 20 mM | 40 mOsm/l |
| 40 mM | 80 mOsm/l |
| 70 mM | 140 mOsm/l |

The reason why the glucose permeability is improved in a case of using the hypertonic aqueous solution (kalium chloride aqueous solution) having a higher osmotic pressure than pure water as an extraction medium is conceivably as follows: In other words, in a case of the pure water medium, a salt concentration of the extraction medium (pure water) is low with respect to a salt concentration in the body, and hence an osmotic pressure of water is lower in a collection reservoir (a portion storing the extraction medium) than in the body, water molecules diffuse into an organism and a solvent flow in a negative direction in which the glucose permeability is reduced is generated. On the other hand, in a case of using the hypertonic aqueous solution (kalium chloride aqueous solution) as an extraction medium, a salt concentration in the collection reservoir is increased and an osmotic pressure of the KCl aqueous solution in this collection reservoir is increased, and hence the solvent flow in a negative direction disappears. Thus, the glucose permeability from the organism to the extraction medium is conceivably improved.

4. Consideration of Type and Concentration of Auxiliary Component

The aforementioned 3. in which the concentration of the auxiliary component (kalium chloride) contained in the hypertonic aqueous solution (kalium chloride aqueous solution) is changed suggested that the glucose permeability is improved by using the hypertonic aqueous solution (kalium chloride aqueous solution) having a higher osmotic pressure than pure water as an extraction medium. In 4., an extraction experiment in which the type and concentration of an auxiliary component contained in the hypertonic aqueous solution are changed was performed under the same measurement conditions as those shown in 3., and more in-depth consideration to conditions allowing improvement of the glucose permeability in a case of using the hypertonic aqueous solution as an extraction medium as compared with a case of using pure water was given.

Specifically, glycine and urea in addition to kalium chloride (KCl) used in the aforementioned 1. and 2. were used as an auxiliary component of the hypertonic aqueous solution. In particular, each experiment was performed with respect to a concentration lower than 5 mM at which an effect of improving the glucose permeability has been confirmed as the concentration of the auxiliary component in each hypertonic aqueous solution. Experiment conditions are as follows:

[Experiment Condition 1]

Auxiliary Component: urea

Auxiliary Component Concentration: 0.3, 0.6, 1.3, 2.5, 5 (mM)

[Experiment Condition 2]

Auxiliary Component: kalium chloride

Auxiliary Component Concentration: 0.4, 0.7, 1.4, 2.9, 5.7 (mM)

[Experiment Condition 3]

Auxiliary Component: glycine

Auxiliary Component Concentration: 0.2, 0.3, 0.7, 1.3, 2.7 (mM)

The remaining experience conditions are the same as those in the aforementioned 3.

A true glucose permeability P'(glc) was calculated from the extraction glucose quantity M(glc) and the blood glucose AUC both obtained by this experiment using the aforementioned formula (6). Further, a glucose permeability ratio P'(glc) ratio was calculated similarly to the aforementioned 3., and a relation between the glucose permeability ratio P'(glc) ratio and the concentration of the auxiliary component in the extraction medium (hypertonic aqueous solution) was evaluated. The results obtained from Experiment Condition 1 (urea), Experiment Condition 2 (kalium chloride) and Experiment Condition 3 (glycine) are shown in FIGS. 44 to 46, respectively.

Figure 44:
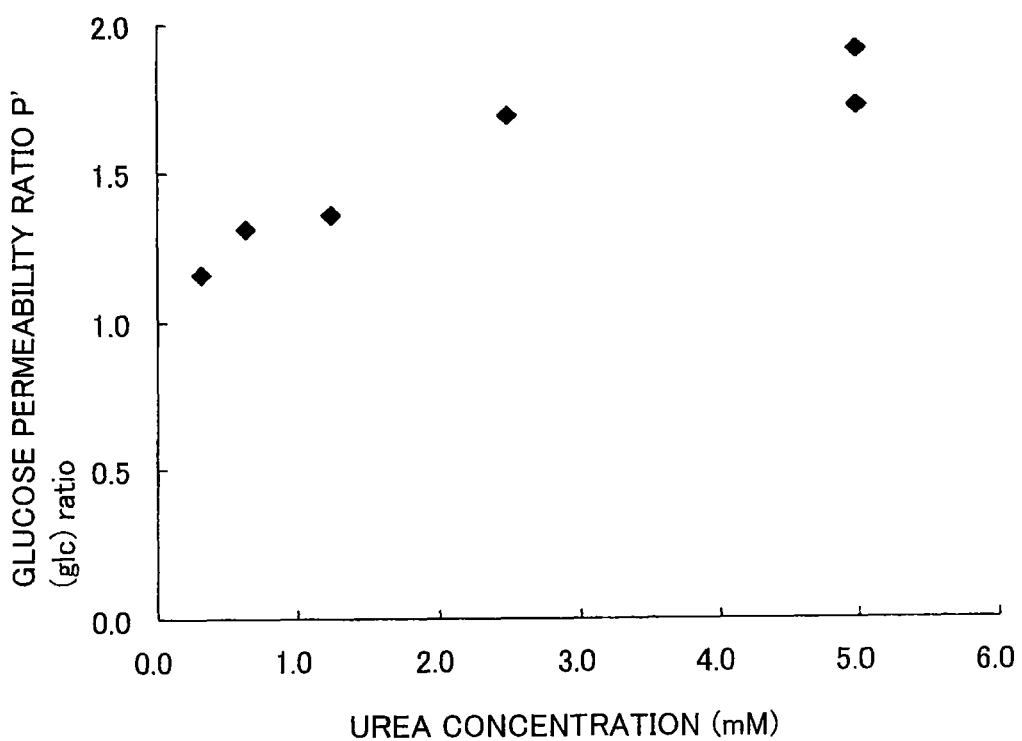
FIG. 44 is a diagram showing dependence of a glucose permeability on a concentration of a urea aqueous solution.

It is clear from FIG. 44 that the glucose permeability is improved as compared with a case of extraction using an extraction medium of pure water when the concentration of urea in the hypertonic aqueous solution (extraction medium) is 0.3 mM or more. Since the P'(glc) ratio is increased from 0.3 mM to 5 mM of the urea concentration, it is suggested that the P'(glc) ratio is increased also in a case of setting the urea concentration at 5 mM or more.

Figure 45:
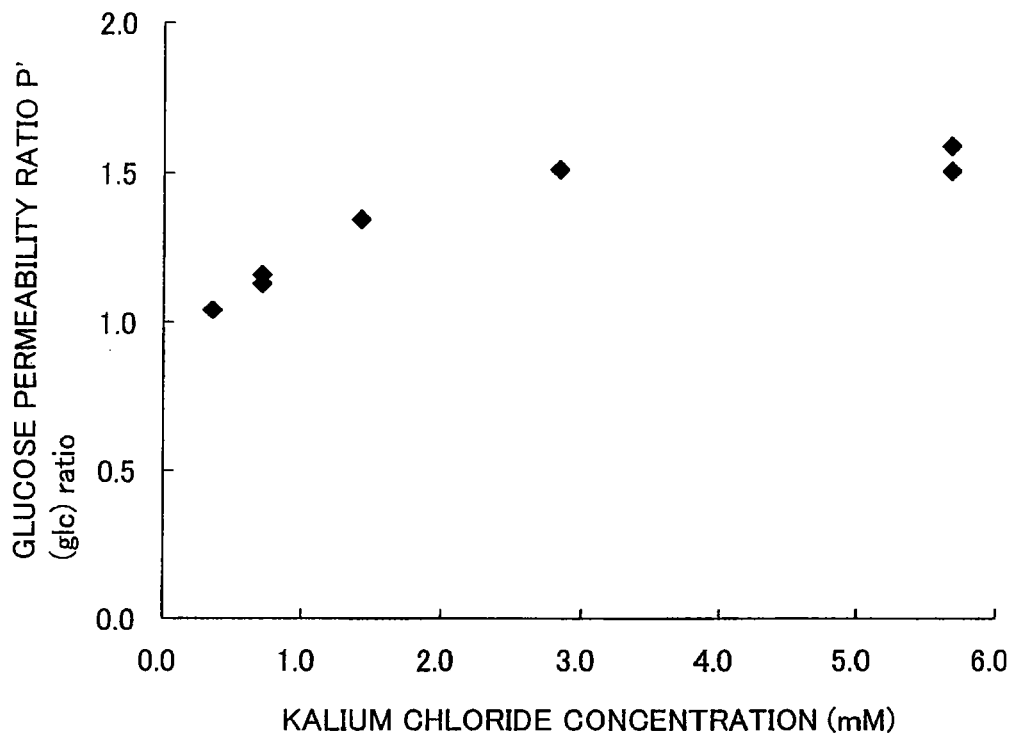
FIG. 45 is a diagram showing dependence of a glucose permeability on a concentration of a kalium chloride aqueous solution.

It is clear from FIG. 45 that the glucose permeability is improved as compared with a case of extraction using an extraction medium of pure water when the concentration of kalium chloride in the hypertonic aqueous solution (extraction medium) is 0.4 mM or more. Further, the P'(glc) ratio is increased from 0.4 mM to 5.7 mM of the kalium chloride concentration. Therefore, it has been clear that the glucose permeability is improved with the increase in the concentration of the auxiliary component (kalium chloride) when increasing the concentration of the kalium chloride.

Figure 46:
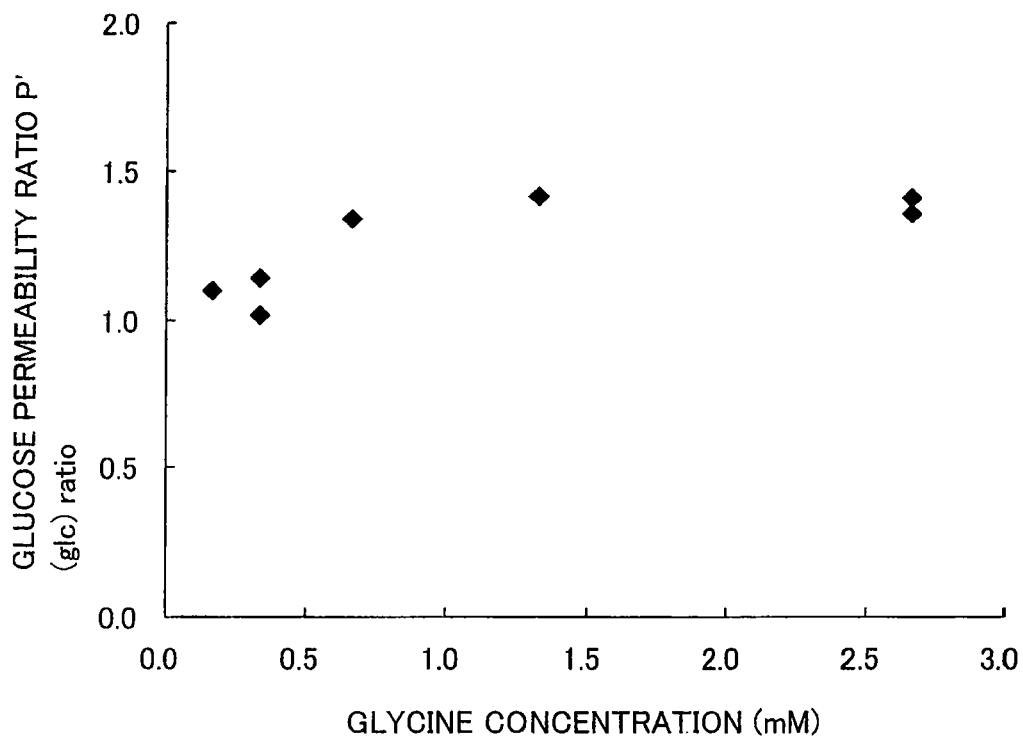
FIG. 46 is a diagram showing dependence of a glucose permeability on a concentration of a glycine aqueous solution.

It is clear from FIG. 46 that the glucose permeability is improved as compared with a case of extraction using an extraction medium of pure water when the concentration of urea in the hypertonic aqueous solution (extraction medium) is 0.3 mM or more. Since the P'(glc) ratio is increased from 0.3 mM to 5 mM of the urea concentration, it is suggested that the P'(glc) ratio is increased also in a case of setting the urea concentration at 5 mM or more.

It is clear from FIG. 45 that the glucose permeability is improved as compared with a case of extraction using an extraction medium of pure water when the concentration of kalium chloride in the hypertonic aqueous solution (extraction medium) is 0.4 mM or more. Further, the P'(glc) ratio is increased from 0.4 mM to 5.7 mM of the kalium chloride concentration. Therefore, it has been clear that the glucose permeability is improved with the increase in the concentration of the auxiliary component (kalium chloride) when increasing the concentration of the kalium chloride.

It is clear from FIG. 46 that the glucose permeability is improved as compared with a case of extraction using an extraction medium of pure water when the concentration of glycine in the hypertonic aqueous solution (extraction medium) is 0.2 mM or more. Since the P'(glc) ratio is increased from 0.2 mM to 2.7 mM of the glycine concentration, it is suggested that the glucose permeability is improved also in a case of setting the glycine concentration at 2.5 mM or more similarly to the aforementioned 3.

In 4., it has been confirmed from these results that the glucose permeability is improved as compared with a case of extraction using pure water as an extraction medium also in a case of using urea and glycine other than kalium chloride as an auxiliary component. Further, it has been confirmed that an effect of improving the glucose permeability is obtained in the concentration of at least 0.2 mM as the concentration of the auxiliary component. It has been verified that the glucose permeability from the organism to the extraction medium is increased due to the increase in the osmotic pressure (concentration) of the hypertonic aqueous solution (KCl aqueous solution) because the glucose permeability was monotonically increased in a case where the concentration of the kalium chloride was increased from 0.4 mM to about 20 mM considering the results in the aforementioned 3.

As described above, it has been verified that movement of the measurement target component (glucose) to the hypertonic aqueous solution can be enhanced by using the hypertonic aqueous solution having a higher osmotic pressure than pure water as an extraction medium in the measurement method according to each of the third and fourth embodiments. Further, it has been verified that movement of the tissue fluid to the hypertonic aqueous solution can be enhanced by using at least one selected from a group consisting of kalium chloride, glycine and urea as an auxiliary component and setting the concentration of this auxiliary component at 0.2 mM or more.

The embodiments and examples disclosed this time must be considered as illustrative in all points and not restrictive. The range of the present invention is shown not by the above description of the embodiments and examples but by the scope of claims for patent, and all modifications within the meaning and range equivalent to the scope of claims for patent are further included.

For example, while the example of measuring a blood glucose AUC has been shown in each of the aforementioned embodiments, another value other than an AUC can be measured so far as it is an integrated value of a concentration of the measurement target component in the organism, corresponding to an extraction time of the tissue fluid. For example, an average value of a glucose concentration in blood within the extraction time of the tissue fluid may be measured.

While the example of using pure water as a collection member has been shown in each of Examples 1 and 2, a similar effect can also be obviously attained by using a gel. A capacity of the pure water or the gel may have a volume allowing glucose in the tissue fluid extracted for 60 minutes or more to be accumulated, and such volume of the gel or the pure water can be calculated as follows:

When glucose permeability P(glc) of a plurality of subjects were calculated, a maximum value of the glucose permeability P(glc)s was predicted to be $5 \times 10^{-6}$ dL/h at best. A maximum value of a blood glucose AUC obtained by extracting the tissue fluid for 180 minutes was predicted to be 800 mg·h/dL at best. Because M(glc)=predicted AUC×P(glc) is obtained from the formula (6), the maximum glucose extraction quantity per 180 minutes of an extraction time is calculated as follow:

$$M\text{max}=5\times10^{-6}(\text{dl/h})\times800(\text{mg})=4.0 \text{ µg}$$

Such a volume V of the gel that a glucose concentration in the gel retaining this maximum glucose extraction quantity becomes not more than 5% (Cmax) of a blood glucose level (80 mg/dL) in the normal fasting state is obtained from Mmax/cmax as follows:

$$4.0 \text{ µg}/(80 \text{ mg/dL} \times 0.05)=1.0\times10^{-4} \text{ L}$$

Thus, a volume of the gel in a case where the extraction time is 180 minutes is preferably 100 µL or more. Further, a volume of the gel in a case where the extraction time is 120 minutes is preferably 100 µL×⅔=66 µl, or more. Similarly, a volume of the gel in a case where the extraction time is 60 minutes is preferably 100 µL×⅓=33 µl or more.

While kalium chloride (KCl), urea and glycine each are used as an auxiliary component for increasing an osmotic pressure of the extraction medium (hypertonic aqueous solution) in each of the aforementioned third and fourth embodiments, the osmotic pressure can be increased and a similar effect can be attained also by using another neutral molecular solvent or electrolyte solvent other than these.

While the example of extracting the tissue fluid from the skin by passive diffusion without applying electricity has been shown in each of the first to fourth embodiments, the tissue fluid may be extracted with electric power by an iontophoresis method when it is not necessary to consider a burden on a subject due to extraction of the tissue fluid for a long time. Even in this case, high voltage application for conducting extraction in a short time is not required in a case where the extraction is conducted for a long time of 60 minutes or more. Thus, a device for applying electricity can be downsized.

While the example of extracting the tissue fluid after enhancing the extraction of the tissue fluid by forming the fine pores 601 by the puncture device 400 has been shown in each of the aforementioned first to fourth embodiments, the present invention is not restricted to this, but the extraction of the tissue fluid may be enhanced by a so-called peeling or like for removing the cuticle of the skin. Alternatively, the extraction of the tissue fluid may be enhanced using an enhancer enhancing permeation of the measurement target component (glucose) from the skin. Alcohol or a surfactant can be used as the enhancer, for example. The enhancer may be applied directly to the skin or may be contained in the gel. Further, it is also appropriate to enhance the extraction of the measurement target component using ultrasound. More specifically, low-frequency ultrasound of about 20 kHz is allowed to act on the skin, whereby a barrier function of the epidermal tissue is reduced, and the extraction of the tissue fluid can be enhanced.

While the example of calculating a predicted blood glucose AUC by correcting a value of the extraction glucose quantity using the extraction rate of an electrolyte (NaCl) in order to reflect opening of the fine pores 601 has been shown in each of the aforementioned first to fourth embodiments, the present invention is not restricted to this, but it is not necessary to correct the value of the extraction glucose quantity using the extraction rate of the electrolyte if the opening of the fine pores can be rendered constant. In this case, the value of the extraction glucose quantity can be used as a predicted blood glucose AUC.

While the example of measuring the extraction rate of an electrolyte (NaCl) in order to reflect opening of the fine pores 601 has been shown in each of the aforementioned first to fourth embodiments, the present invention is not restricted to this, but no electrolyte may be used so far as a substance plentifully contained in the tissue fluid is used.

While the example of using a gel made of polyvinyl alcohol as each of the gels 301 and 801 has been shown in each of the aforementioned first and third embodiments, the present invention is not restricted to this, but a gel made of cellulose or polyacrylic acid may be used.

While the example of calculating a predicted blood glucose AUC serving as a value corresponding to a blood drawing blood glucose AUC, which is an index used to grasp clinical conditions of a diabetic subject, has been shown in each of the aforementioned first and second embodiments, the present invention is not restricted to this, but a value obtained by the measurement method of the present invention may be used to grasp clinical conditions of another disease.

While the example of measuring the glucose quantity in the tissue fluid has been shown in each of the aforementioned first and second embodiments, the present invention is not restricted to this, but the amount of substances, other than glucose, contained in the tissue fluid may be measured. The substances measured according to the present invention include biochemical components, drugs taken into a subject and so on, for example. The biochemical components include albumin, globulin, enzyme and so on, each of which is protein, a biochemical component. The biochemical components other than protein include creatinine, creatine, uric acid, amino acid, fructose, galactose, pentose, glycogen, lactic acid, pyruvic acid, ketone body and so on. The drugs include digitalis preparation, theophylline, arrhythmic drug, antiepileptic drug, aminoglycoside antibiotic, glycopeptide antibiotic, antithrombotic drug, immunosuppressant drug and so on.

While the example of displaying a value of a calculated predicted blood glucose AUC as it is on the display portion 1 has been shown in the aforementioned first embodiment, the present invention is not restricted to this, but a value obtained by dividing the value of the calculated predicted blood glucose AUC by the extraction time may be displayed on the display portion 1. Thus, a predicted blood glucose AUC per unit time can be obtained, and hence those values can be easily compared with each other even in a case where the extraction times are different from each other.

Figure 47:
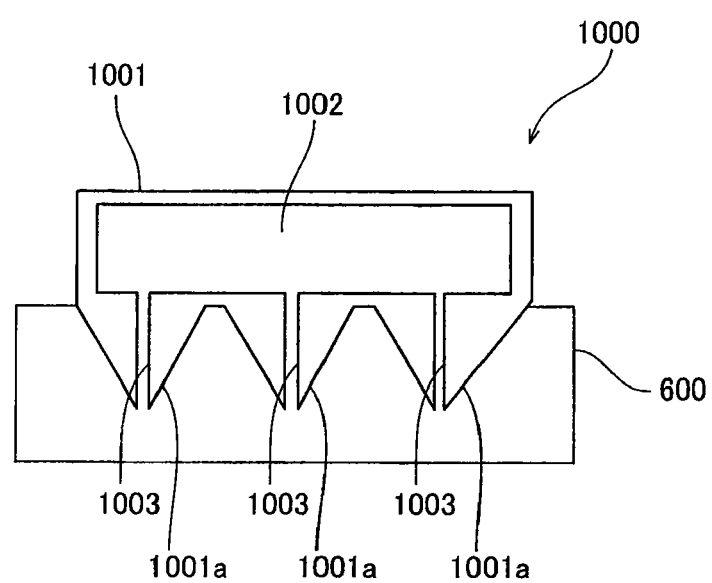
FIG. 47 is a schematic view showing a reservoir according to a modification of each of the first to fourth embodiments of the present invention.

While the example of forming fine pores and applying the gel to the skin where the fine pores are formed has been shown in each of the aforementioned embodiments, the present invention is not restricted to this, but a collection reservoir 1000 shown in FIG. 47 may be used. More specifically, the collection reservoir 1000 in which a fine needle chip 1001 and a gel 1002 are integrated with each other and hollow portions 1003 leading to the gel 1002 from ends of fine needles 1001a are provided is used. This collection reservoir 1000 is brought into contact with the skin 600 and is left in a state where the fine needles 1001a pass through the cuticle of the skin 600 as shown in FIG. 47, whereby tissue fluid in the skin 600 moves from the ends of the fine needles 1001a to the gel 1002 through the hollow portions 1003 by capillarity and is accumulated in the gel 1002.

While the quantity of glucose is determined with a current value in oxidizing the glucose by a GOD enzyme measurement method in each of the aforementioned embodiments, the quantity of glucose may be determined based on a change of coloring of pigment by allowing glucose to act on a reaction system in which GOD and peroxidase exist together. Further, the absorbance is measured by applying light of a specific wavelength, which glucose efficiently absorbs, to the gel or pure water, and the amount of glucose may be determined based on the absorbance.

While glucose contained in the extracted tissue fluid is accumulated in the gel and the quantity of the accumulated glucose is determined in each of the aforementioned embodiments, the glucose in the extracted tissue fluid may be converted into another chemical substance to be accumulated and the quantity of the chemical substance into which the glucose is converted may be determined. For example, there is an example of containing glucose oxidase (GOD), peroxidase (POD) and chromogen in the gel 301.

According to this structure, the following chemical reaction is caused in the gel 301, and a color of the gel 301 changes.

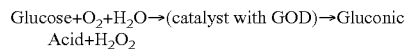
Glucose+$O_2$+$H_2O$→(catalyst with GOD)→Gluconic Acid+$H_2O_2$

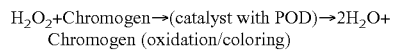
$H_2O_2$+Chromogen→(catalyst with POD)→$2H_2O$+ Chromogen (oxidation/coloring)

The degree of coloring of chromogen is proportional to the quantity of glucose, and hence colorimetric determination is made on the gel after the extraction of the tissue fluid for a prescribed time, whereby the quantity of the glucose can be determined.

What is claimed is:

1. An in vivo component measurement method, comprising:
    preparing tissue fluid extracted for an extract time of 60 minutes or more from an organism on which a treatment for enhancing extraction of tissue fluid has been made;
    acquiring, using a detection portion of an in vivo component measurement apparatus, a value relating to an amount of a measurement target component in the extracted tissue fluid;
    acquiring a value relating to an amount of an electrolyte contained in the extracted tissue fluid; and
    acquiring, using an analysis portion of the in vivo component measurement apparatus, a value corresponding to an area under the curve (AUC) of a blood concentration time curve of the measurement target component corresponding to the extraction time of 60 minutes or more based on the value relating to the amount of the measurement target component, the value relating to the amount of the electrolyte, and the extraction time of 60 minutes or more.

2. The in vivo component measurement method according to claim 1, wherein
    the treatment is made by forming fine pores on a skin of the organism, and
    the extraction is performed through the skin where the fine pores are formed.

3. The in vivo component measurement method according to claim 1, wherein the extraction is performed by extracting tissue fluid to an extraction medium containing a hypertonic aqueous solution having a higher osmotic pressure than pure water.

4. The in vivo component measurement method according to claim 3, wherein
the hypertonic aqueous solution contains an auxiliary component different from the measurement target component, the auxiliary component being contained with the measurement target component in the tissue fluid.

5. The in vivo component measurement method according to claim 4, wherein
the auxiliary component is at least one selected from a group consisting of kalium chloride, glycine and urea.

6. The in vivo component measurement method according to claim 5, wherein
the auxiliary component is contained in a concentration of 0.2 mmol/L or more in the hypertonic aqueous solution.

7. The in vivo component measurement method according to claim 1, wherein
the extraction time is 120 minutes or more.

8. The in vivo component measurement method according to claim 1, wherein
the extraction time is 180 minutes or more.

9. The in vivo component measurement method according to claim 1, wherein
the measurement target component is glucose.

10. The in vivo component measurement method according to claim 1, further comprising acquiring a value obtained by dividing the value corresponding to the AUC of the measurement target component by the extraction time.

11. The in vivo component measurement method according to claim 1, further comprising informing a subject of an end of extraction when the extraction time of 60 minutes or more elapses from a start of extraction of the tissue fluid.

12. An in vivo component measurement apparatus, comprising:
a set portion for setting a collection member accumulating tissue fluid extracted for an extraction time of 60 minutes or more from an organism on which a treatment for enhancing extraction of tissue fluid has been made;
a detection portion for acquiring a value relating to an amount of a measurement target component contained in the tissue fluid accumulated by the collection member set on the set portion and a value relating to an amount of an electrolyte contained in the tissue fluid accumulated by the collection member set on the set portion; and
an analysis portion acquiring a value corresponding to an area under the curve (AUC) of a blood concentration time curve of the measurement target component corresponding to the extraction time of 60 minutes or more based on the value relating to the amount of the measurement target component, the value relating to the amount of the electrolyte, and the extraction time of 60 minutes or more.

13. The in vivo component measurement apparatus according to claim 12, wherein
the extraction time is 120 minutes or more.

14. The in vivo component measurement apparatus according to claim 12, wherein
the extraction time is 180 minutes or more.

15. The in vivo component measurement apparatus according to claim 12, wherein
the measurement target component is glucose.

16. A data processing method for in vivo component measurement, comprising:
acquiring a value relating to an amount of a measurement target component in tissue fluid extracted for an extraction time of 60 minutes or more from an organism on which a treatment for enhancing extraction of tissue fluid has been made;
acquiring, using a detection portion of an in vivo component measurement apparatus, a value relating to an amount of an electrolyte contained in the extracted tissue fluid; and
acquiring, using an analysis portion of the in vivo component measurement apparatus, a value corresponding to an area under the curve (AUC) of a blood concentration time curve of the measurement target component corresponding to the extraction time of 60 minutes or more based on the value relating to the amount of the measurement target component, the value relating to the amount of the electrolyte, and the extraction time of 60 minutes or more.

17. The data processing method for in vivo component measurement according to claim 16, wherein the extraction time is 120 minutes or more.

18. The data processing method for in vivo component measurement according to claim 16, wherein
the extraction time is 180 minutes or more.

19. The data processing method for in vivo component measurement according to claim 16, wherein
the measurement target component is glucose.

\* \* \* \* \*